United States Patent [19]

Bradshaw et al.

[11] Patent Number: 5,358,948

[45] Date of Patent: Oct. 25, 1994

[54] BENZANILIDE DERIVATIVES

[75] Inventors: John Bradshaw; John W. Clitherow, both of Ware, Great Britain

[73] Assignee: Glaxco Group Limited, London, England

[21] Appl. No.: 946,099

[22] Filed: Sep. 17, 1992

[30] Foreign Application Priority Data

Sep. 18, 1991 [GB] United Kingdom ............ 9119932.3

[51] Int. Cl.$^5$ .................. A61K 31/495; C07D 401/00
[52] U.S. Cl. ..................................... 514/252; 544/360
[58] Field of Search ..................... 544/360; 514/252

[56] References Cited

U.S. PATENT DOCUMENTS 3,192,213  6/1965  Krapcho ............................ 260/253
4,058,523  11/1977 Mori et al. ........................ 544/165
4,735,959  4/1988  Grell et al. ....................... 514/357

FOREIGN PATENT DOCUMENTS

86/67002  7/1987  Australia .
0058779  9/1982  European Pat. Off. .
0210782  2/1987  European Pat. Off. .
0310370  4/1989  European Pat. Off. .
0324521  7/1989  European Pat. Off. .
0365064  4/1990  European Pat. Off. .
2545978  4/1976  Fed. Rep. of Germany .
63-258446 10/1988 Japan .
1157586  7/1969  United Kingdom .
84/00545  2/1984  World Int. Prop. O. .

OTHER PUBLICATIONS

Charles et al., *Archiv der Pharmazie,* vol. 315, No. 2, pp. 97–103, Feb. 1982.
Waeber et al., *Neurochemical Research* vol. 15, (1990), pp. 573–588.
Fillion et al., *Adv. Exp. Med. Biol.* 236, (1988) pp. 313–328.

*Primary Examiner*—Cecilia Tsang
*Attorney, Agent, or Firm*—Bacon & Thomas

[57] ABSTRACT

The invention provides compounds of formula (I):

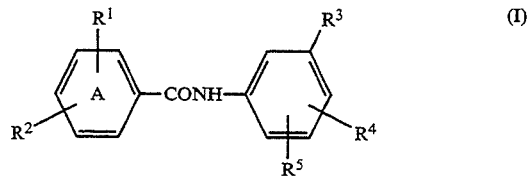

or a physiologically acceptable salt or solvate thereof wherein $R^1$ represents a hydrogen atom, a halogen atom or a group selected from $C_{1-6}$alkyl and $C_{1-6}$alkoxy;

$R^2$ represents a pyridinyl group optionally substituted by one or two substituents selected from halogen atoms, $C_{1-6}$alkyl, hydroxy$C_{1-6}$alkyl, $C_{1-6}$alkoxy$C_{1-6}$alkyl, $C_{1-6}$alkoxy, hydroxy, —CN, —NO$_2$, —CO$_2^6$, —COR$^6$, —CONR$^6$R$^7$ and —(CH$_2$)$_m$OC(O)C$_{1-4}$alkyl;

$R^3$ represents the group

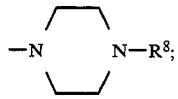

$R^4$ and $R^5$ which may be the same or different, each independently represent a hydrogen atom or a halogen atom or a group selected from hydroxy, $C_{1-6}$alkoxy and $C_{1-6}$alkyl;

$R^6 R^7$ and $R^8$, which may be the same or different, each independently represent a hydrogen atom or a $C_{1-6}$alkyl group; and m represents zero or an integer from 1 to 3.

The compounds may be used in the treatment or prophylaxis of depression and other CNS disorders.

23 Claims, No Drawings

BENZANILIDE DERIVATIVES

This invention relates to novel benzanilide derivatives, to processes for their preparation, and to pharmaceutical compositions containing them.

According to the invention we provide compounds of the general formula (I):

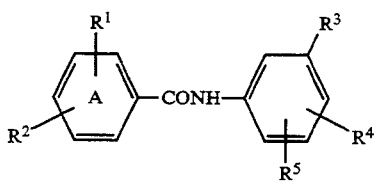

or a physiologically acceptable salt or solvate (eg hydrate) thereof, in which $R^1$ represents a hydrogen atom, a halogen atom or a group selected from $C_{1-6}$alkyl and $C_{1-6}$alkoxy;

$R^2$ represents a pyridinyl group optionally substituted by one or two substituents selected from halogen atoms, $C_{1-6}$alkyl, hydroxy$C_{1-6}$alkyl, $C_{1-6}$alkoxy$C_{1-6}$alkyl, $C_{1-6}$alkoxy, hydroxy, —CN, —$NO_2$, —$CO_2R^6$, —$COR^6$, —$CONR^6R^7$ and —$(CH_2)_mOC(O)C_{1-4}$alkyl;

$R^3$ represents the group

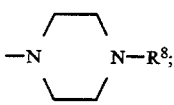

$R^4$ and $R^5$, which may be the same or different, each independently represent a hydrogen atom or a halogen atom or a group selected from hydroxy, $C_{1-6}$alkoxy and $C_{1-6}$alkyl;

$R^6$, $R^7$ and $R^8$, which may be the same or different, each independently represent a hydrogen atom or a $C_{1-6}$alkyl group; and m represents zero or an integer from 1 to 3.

It is to be understood that the present invention encompasses all geometric and optical isomers of the compounds of general formula (I) and their mixtures including the racemic mixtures thereof.

Physiologically acceptable salts of the compounds of general formula (I) include acid addition salts formed with inorganic or organic acids (for example hydrochlorides, hydrobromides, sulphates, phosphates, benzoates, naphthoates, hydroxynaphthoates, p-toluenesulphonates, methanesulphonates, sulphamates, ascorbates, tartrates, citrates, oxalates, maleates, salicylates, fumarates, succinates, lactates, glutarates, glutaconates, acetates or tricarballylates) and, where appropriate, inorganic base salts such as alkali metal salts (for example sodium salts).

In the compounds of general formula (I), the term '$C_{1-6}$alkyl' or '$C_{1-6}$alkoxy' as a group or part of a group means that the group is straight or branched and consists of 1 to 6 carbon atoms. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy. The term 'halogen' within the definition of $R^2$ means fluorine, chlorine, bromine or iodine.

A preferred group of compounds of general-formula (I) is that wherein $R^2$ is a 3-pyridinyl, or more preferably a 4-pyridinyl, group optionally substituted by one or two substituents as defined in general formula (I).

Another preferred group of compounds of general formula (I) is that wherein $R^2$ is a pyridinyl group optionally substituted by a single substituent, in particular a $C_{1-6}$alkyl, especially methyl, group. Particularly preferred are those compounds wherein the substituent on the pyridinyl group is in a position ortho to the bond to the phenyl ring A in general formula (I).

A further preferred group of compounds of general formula (I) is that wherein $R^1$ is a hydrogen atom, a halogen atom, especially a fluorine atom, or a group selected from $C_{1-3}$alkyl, especially methyl, and $C_{1-3}$alkoxy, especially methoxy.

Another preferred group of compounds of general formula (I) is that wherein $R^4$ is attached in the para-position relative to the amide linkage.

A further preferred group of compounds of general formula (I) is that wherein $R^4$ is a hydrogen atom or a halogen atom, especially chlorine or fluorine, or a group selected from hydroxy, $C_{1-3}$alkoxy, especially methoxy, and $C_{1-3}$alkyl, especially methyl.

Also preferred is the group of compounds of general formula (I) wherein $R^5$ is a hydrogen atom or a $C_{1-6}$alkoxy, especially methoxy, group, particularly, $R^5$ is a hydrogen atom.

A yet further preferred group of compounds of general formula (I) is that wherein $R^8$ is a hydrogen atom or a $C_{1-3}$alkyl, especially methyl, group.

Compounds of general formula (I) wherein $R^4$ represents a hydroxy or methoxy group, $R^5$ represents a hydrogen atom and $R^8$ represents a methyl group are particularly preferred.

Particularly preferred compounds of general formula (I) include:
N-[4-methoxy-3-(4-methyl-1-piperazinyl)phenyl]-4-(4-pyridinyl) benzamide;
N-[4-methoxy-3-(4-methyl-1-piperazinyl)phenyl]-4-(4-methyl-3-pyridinyl)benzamide;
N-[4-methoxy-3-(4-methyl-1-piperazinyl)phenyl]-3-methyl-4-(4-pyridinyl)benzamide;
and their physiologically acceptable salts and solvates.

Further preferred compounds of general formula (I) include:
N-[4-methoxy-3-(4-methyl-1-piperazinyl)phenyl]-2-methyl-4-(4-pyridinyl)benzamide;
N-[4-methyl-3-(4-methyl-1-piperazinyl)phenyl]-4-(4-pyridinyl)benzamide;
N-[4-chloro-3-(4-methyl-1-piperazinyl)phenyl]-4-(4-pyridinyl)benzamide;
N-[4-fluoro-3-(4-methyl-1-piperazinyl)phenyl]-4-(4-pyridinyl)benzamide;
N-[4-methoxy-3-(4-methyl-1-piperazinyl]-4-(3.-methyl-4-pyridinyl)benzamide;
N-[6-fluoro-4-methoxy-3-(4-methyl-1-piperazinyl)-phenyl]-3-methyl-4-(4-pyridinyl)benzamide;
N-[4-bromo-3-(4-methyl-1-piperazinyl)phenyl]-3-methyl-4-(4-pyridinyl)benzamide;
N-[3-(4-methyl-1-piperazinyl)phenyl]-4-(4-pyridinyl)-benzamide;
4-(4-pyridinyl)-2-methoxy-N-[4-methoxy-3-(4-methyl-1-piperazinyl) phenyl]benzamide;
N-[4-hydroxy-3-(4-methyl-1-piperazinyl)phenyl]4-(4-pyridinyl) benzamide;
and their physiologically acceptable salts and solvates.

5-Hydroxytryptamine (serotonin) is a neurotransmitter which is widely distributed within the central nervous system (CNS), platelets and the gastrointestinal tract. Changes in transmission in serotonergic pathways in the CNS are known to modify, for example, mood, psychomotor activity, appetite, memory and blood pressure. Release of 5-hydroxytryptamine from platelets can mediate vasospasm while changes in free 5-hydroxytryptamine levels in the gastrointestinal tract can modify secretion and motility.

Abundant pharmacological studies have led to the discovery of multiple types of receptors for 5-hydroxytryptamine, thus providing a molecular basis to the diversity of its actions. These receptors are classed as 5-HT$_1$, 5-HT$_2$ and 5-HT$_3$, with 5-HT$_1$ receptors being sub-classified as 5-HT$_{1A}$, 5-HT$_{1B}$, 5-HT$_{1C}$, 5-HT$_{1D}$ and 5-HT$_{1D}$ (like) receptors. The identification of these classes and sub-classes of receptor is based mainly on radiological binding studies.

Compounds having a selective antagonist action at 5-HT$_{1D}$ receptors such as those described herein may exhibit a beneficial effect on subjects suffering from CNS disorders.

Accordingly, in a further aspect of the present invention, there is provided a method of treating a patient suffering from a CNS-disorder, which method comprises administering to the patient an effective amount of a 5-HT$_{1D}$ antagonist. The patient is preferably a human patient.

In another aspect of the present invention, there is provided a 5-HT$_{1D}$ antagonist for use in the manufacture of a medicament for the treatment of a CNS disorder.

In the present specification, a 5-HT$_{1D}$ antagonist is a non-naturally occurring (synthetic) compound that specifically and selectively antagonises 5-HT$_{1D}$ receptors, i.e. —blocks the specific actions of 5-hydroxytryptamine mediated by the 5-HT$_{1D}$ receptor. Such compounds may be identified by a high level of affinity (pKi$\geq$8) in the in vitro human cortex and guinea-pig striatum radioligand binding assays described by Hoyer et al, Neuroscience Letters, 1988, 85, p357–362. Activity at 5-HT$_{1D}$ receptors may be confirmed in vivo using the guinea pig rotation model described by G A Higgins et al, *Br. J. Pharmacol.*, 1991, 102, p305–310.

A 5-HT$_{1D}$ antagonist for use in the present method of treatment must be selective for 5-HT$_{1D}$ receptors. In the present specification, this means that the 5-HT$_{1D}$ antagonist must be 30 or more times more selective for 5-HT$_{1D}$ receptors than 5-HT$_{1A}$, 5-HT$_{1C}$ or 5-HT$_2$ receptors.

According to this definition the affinity of a compound for 5-HT$_{1A}$, 5-HT$_{1C}$ and/or 5-HT$_2$ receptors is measured using the in vitro tests described in the following publications:

5-HT$_{1A}$: Gozlan et al, Nature, 1983, 305, p140–142
5-HT$_{1C}$: Pazos et al, Eur. J. Pharmacol., 1984, 106, p531–538
5-HT$_{2A}$: Humphrey et al, Br. J. Pharmacol, 1988, 94, p1123–1132 (rabbit aorta model).

Thus, for example, compounds of the present invention have been shown to inhibit 5-hydroxytryptamine induced contraction of the dog isolated saphenous vein and to antagonise the 5-hydroxytryptamine induced inhibition of neurotransmission in central and peripheral neurones.

5-HT$_{1D}$ Antagonists, and in particular the compounds of the present invention, may therefore be of use in the treatment of CNS disorders such as mood disorders, including depression, seasonal affective disorder and dysthymia; anxiety disorders, including generalised anxiety, panic disorder, agoraphobia, social phobia, obsessive compulsive disorder and post-traumatic stress disorder; memory disorders, including dementia, amnestic disorders and age-associated memory impairment; and disorders of eating behaviour, including anorexia nervosa and bulimia nervosa. Other CNS disorders include Parkinson's disease, dementia in Parkinson's disease, neuroleptic-induced parkinsonism and tardive dyskinesias, as well as other psychiatric disorders.

5-HT$_{1D}$ Antagonists, and in particular compounds of the present invention, may also be of use in the treatment of endocrine disorders such as hyperprolactinaemia, in the treatment of vasospasm (particularly in the cerebral vasculature) and hypertension, as well as disorders in the gastrointestinal tract where changes in motility and secretion are involved. They may also be of use in the treatment of sexual dysfunction.

Therefore, according to a second aspect of the invention, we provide a compound of general formula (I) or a physiologically acceptable salt or solvate thereof for use in therapy.

According to a further aspect of the present invention, we therefore provide a compound of general formula (I) or a physiologically acceptable salt or solvate thereof for use in the treatment of the aforementioned disorders.

According to another aspect of the invention, we provide the use of a compound of general formula (I) or a physiologically acceptable salt or solvate thereof for the manufacture of a therapeutic agent for the treatment of the aforementioned disorders.

According to a further aspect of the invention, we provide, a method of treating the aforementioned disorders which comprises administering an effective amount to a patient in need of such treatment of a compound of general formula (I) or a physiologically acceptable salt or solvate thereof.

In particular, according to another aspect of the invention, we provide a compound of general formula (I) or a physiologically acceptable salt or solvate thereof for use in the treatment or prophylaxis of depression.

It will be appreciated that the compounds according to the invention may advantageously be used in conjunction with one or more other therapeutic agents, for instance, different antidepressant agents such as tricyclic antidepressants (e.g. amitriptyline, dothiepin, doxepin, trimipramine, butriptyline, clomipramine, desipramine, imipramine, iprindole, lofepramine, nortriptyline or protriptyline), monoamine oxidase inhibitors (e.g. isocarboxazid, phenelzine or tranylcyclopramine) or 5-HT reuptake inhibitors (e.g. fluvoxamine, sertraline, fluoxetine or paroxetine), and/or antiparkinsonian agents such as dopaminergic antiparkinsonian agents (e.g. levodopa, preferably in combination with a peripheral decarboxylase inhibitor e.g. benserazide or carbidopa, or a dopamine agonist e.g. bromocriptine, lysuride or pergolide). It is to be understood that the present invention covers the use of a compound of general formula (I) or a physiologically acceptable salt or solvate thereof in combination with one or more other therapeutic agents.

Thus there is provided in a further or alternative aspect of the present invention a compound of general formula (I) or a physiologically acceptable salt or solvate thereof and an antidepressant agent in the presence of each other in the human or non-human animal body for use in the treatment of the aforementioned disorders.

In a particular aspect of the present invention there is provided a compound of general formula (I) or a physiologically acceptable salt or solvate thereof and an antiparkinsonian agent such as a dopaminergic antiparkinsonian agent, e.g. levodopa, and a peripheral decarboxylase inhibitor, e.g. benserazide or carbidopa, or a dopamine agonist e.g. bromocriptine, lysuride or pergolide, in the presence of each other in the human or non-human animal body for use in the treatment of Parkinson's disease, dementia in parkinsonism, neuroleptic induced parkinsonism and tardive dyskinesias.

In using a compound of general formula (I) or a physiologically acceptable salt or solvate thereof and one or more therapeutic agents it may be preferable to employ the active ingredients in the form of separate pharmaceutical formulations- A combined formulation can be used, however, in such a combined formulation the active ingredients must of course be stable and mutually compatible in the particular formulation employed.

It will be appreciated that administration o#the active ingredients to a human or non-human patient may be simultaneous, separate or sequential. Where administration is not simultaneous, the delay in administering the second of the active ingredients should not be such as to lose the beneficial effect of the combination.

While it is possible that a compound of general formula (I) may be administered as the raw chemical it is preferable to present the active ingredient as a pharmaceutical formulation.

The compounds of general formula (I) and their physiologically acceptable salts and solvates may be formulated for administration in any convenient way, and the invention therefore also includes within its scope pharmaceutical compositions comprising at least one compound of general formula (I) or a physiologically acceptable salt or solvate thereof. Such compositions may be presented for use in a conventional manner in admixture with one or more physiologically acceptable carriers or excipients.

The carrier(s) must be "acceptable" in the sense of being compatible with the other ingredients of the formulation and not deleterious to the recipient thereof.

Thus, the compositions according to the invention may be formulated for oral, buccal, parenteral or rectal administration or in a form suitable for administration by inhalation or insufflation. Oral administration is preferred.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcrystalline cellulose maize-starch, calcium phosphate or sorbitol; lubricants, for example, magnesium stearate, stearic acid, talc, polyethylene glycol or silica; disintegrants, for example, potato starch or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methylcellulose, glucose/sugar syrup, gelatin, hydroxypropyl methylcellulose, carboxymethylcellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by bolus injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation either orally or nasally the compositions according to the invention are conveniently delivered in the form of an aerosol spray presentation from pressurised packs with the use of a suitable propellant, e.g. dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation the compositions according to the invention may take the form of a dry powder composition, for example a powder mix of the compound and a suitable powder base such as lactose or starch. The powder composition may be presented in unit dosage form in, for example, capsules or cartridges of e.g. gelatin, or blister packs from which the powder may be administered with the aid of an inhaler or insufflator.

The pharmaceutical formulations according to the invention may also contain other active ingredients such as antimicrobial agents, or preservatives.

The compositions according to the invention may be prepared by mixing the various ingredients using conventional means.

It will be appreciated that the amount of a compound of general formula (I) required for use in treatment will vary not only with the particular compound selected but also with the route of administration, the nature of the condition being treated and the age and condition of the patient and will ultimately be at the discretion of the attendant physician or veterinarian. In general, however, a proposed dose of the compounds of the invention for administration in man is 0.5 to 1000mg, preferably 1 to 200 mg of the active ingredient per unit dose which could be administered, for example, 1 to 4 times per day.

The compounds of the invention may be prepared by a number of processes as described in the following. In describing the processes which may be used for preparing the compounds of general formula (I) or intermediates useful in the preparation thereof, any of $R^1$–$R^8$ and m in the various formulae are as defined in formula (I) unless otherwise stated.

It will be appreciated that in the following methods for the preparation of compounds of general formula (I), for certain reaction steps it may be necessary to protect various reactive substituents in the starting materials for a particular reaction and subsequently to remove the protecting group. Such protection and subsequent deprotection may be particularly pertinent where $R^6$, $R^7$ and/or $R^8$ in intermediates used to prepare compounds of general formula (I) are hydrogen atoms. Standard protection and deprotection procedures can be employed, for example formation of a phthalimide (in the case of a primary amine), benzyl, trityl, benzyloxycarbonyl or trichloroethoxycarbonyl derivatives. Subsequent removal of the protecting group is achieved by conventional procedures. Thus a phthalimide group may be removed by treatment with hydrazine or a primary amine, for example methylamine. Benzyl or benzyloxycarbonyl groups may be removed by hydrogenolysis in the presence of a catalyst e.g. palladium, and trichloroethoxycarbonyl derivatives may be removed by treatment with zinc dust. Trityl groups may be removed under acidic conditions using standard procedures.

It may also be necessary in some cases to protect carboxylic acid groups (e.g. as esters) or aldehyde or ketone groups (e.g. as acyclic or cyclic acetals or ketals or as thioacetals or thioketals). Subsequent removal of these protecting groups is achieved by conventional procedures. Thus for example alkyl esters may be removed under conditions of acidic or basic hydrolysis, benzyl esters may be removed by hydrogenolysis in the presence of a catalyst e.g. palladium. Acyclic or cyclic acetals or ketals may be removed under conditions of acidic hydrolysis and thioacetals and thioketals may be removed using a mercuric salt.

Hydroxyl groups may also need protection and these may be adequately protected under amenable conditions as their esters or trialkylsilyl, tetrahydropyran and benzyl ethers. Such derivatives may be deprotected by standard procedures.

According to one general process (1), the compounds of general formula (I) may be prepared by a carbonylation reaction involving an aniline (II)

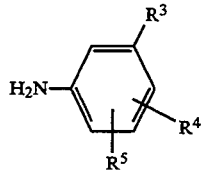

(II)

(where $R^3$, $R^4$ and $R^5$ are as defined in general formula (I)) and a halophenyl compound (III)

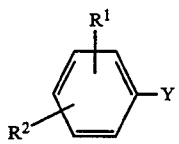

(III)

(where Y represents a halogen atom e.g. bromine or iodine or the group —OSO$_2$CF$_3$, and $R^1$ and $R^2$ are as defined in general formula (I)).

The reaction takes place, for example, in the presence of carbon monoxide using a palladium salt as a catalyst. The reaction is effected in the presence of a suitable base e.g. a trialkylamine such as triethylamine or tri-n-butylamine and may be conducted in a suitable solvent such as an amide e.g. dimethylformamide or a nitrile eg acetonitrile at a temperature within the range of −10° C. to +150° C.

Suitable palladium salts for the reaction include triarylphosphine palladium (II) salts such as bis(triphenylphosphine)palladium (II) chloride.

According to another general process (2), the compounds of general formula (I) may be prepared by treating a compound of formula (IV)

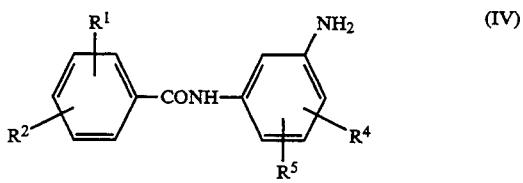

(IV)

with an amine dihalide of formula (V)

$$R^8N(CH_2CH_2Hal)_2 \quad (V)$$

(where Hal is a chlorine, bromine or iodine atom).

The reaction may conveniently take place in the presence of a polar solvent such as an alcohol (e.g. n-butanol) or a nitrile (e.g acetonitrile), optionally in the presence of a base, for example, an alkali metal carbonate such as sodium carbonate or potassium carbonate, or alternatively in a non-polar solvent (e.g. chlorobenzene) in the absence of a base. The reactions may conveniently be carried out at an elevated temperature, for example, reflux.

According to another general process (3), the compounds of general formula (I) may be prepared by reacting an aniline of formula (II) with an activated carboxylic acid derivative of formula (VI)

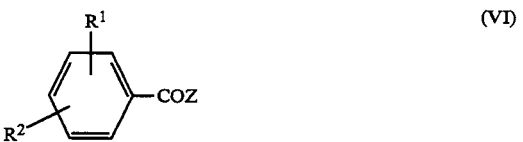

(VI)

(where Z is a leaving group).

Suitable activated carboxylic acid derivatives represented in formula (VI) include acyl halides (e.g. acid chlorides) and acid anhydrides including mixed anhydrides (e.g. acid formic anhydride). These activated derivatives may be formed from the corresponding acid of formula (VII)

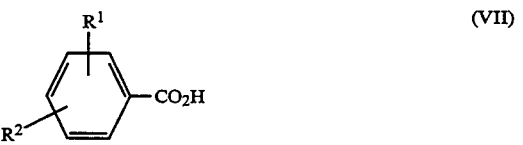

(VII)

by well known procedures. For example, acid chlorides may be prepared by reaction with phosphorus pentachloride, thionyl chloride or oxalyl chloride and acid anhydrides may be prepared by reaction with an appropriate acid anhydride (e.g. trifluoroacetic anhydride), an acid chloride (e.g. acetyl chloride), an alkyl or aralkyl haloformate (e.g. ethyl or benzyl chloroformate) or methanesulphonyl chloride.

Activated carboxylic acid derivatives of formula (VI) may also be prepared in situ by the reaction of the corresponding acids of formula (VII), with a coupling reagent such as carbonyldiimidazole, dicyclohexylcarbodiimide or diphenylphosphorylazide.

The conditions under which the activated carboxylic acid derivatives of formula (VI) are formed and subsequently reacted with the anilines of formula (II) will depend upon the nature of the activated derivative. However, in general the reaction between the compounds (II) and (VI) may be carried out in a non-aqueous medium such as, for example, dimethylformamide, tetrahydrofuran, acetonitrile or a halohydrocarbon such as dichloromethane at a temperature within the range −25° C. to +150° C. The reaction may optionally be carried out in the presence of a base such as triethylamine or pyridine and the base may also be used as the solvent for reaction.

Where acid chlorides are used, the reaction may be carried out using the Schotten-Baumann technique in the presence of a suitable base, for example, aqueous sodium hydroxide, conveniently at a temperature between 0° C. and 100° C., for example, room temperature.

According to another general process (4a), the compounds of general formula (I) may be prepared by treating a compound of formula (VIIIa)

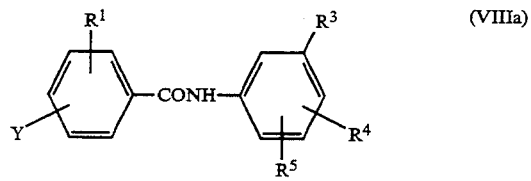

(where Y represents a bromine or iodine atom or the group —OSO$_2$CF$_3$) with a compound of formula (IXa)

or an ester or an anhydride thereof.

Alternatively, according to the general process: (4b), the compounds of general formula (I) may be prepared by treating a compound of formula (VIIIb)

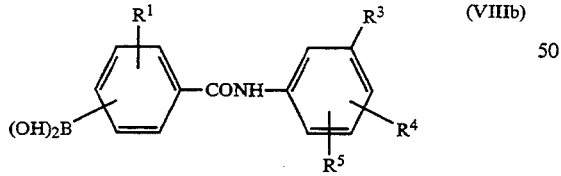

or an ester or an anhydride thereof, with a compound of formula (Ixb)

where Y represents a bromine or iodine atom or the group —OSO$_2$CF$_3$.

Both reactions may be effected in the presence of a transition metal catalyst such as (Ph$_3$P)$_4$Pd (where Ph represents phenyl) in a suitable solvent such as an ether (eg 1,2-dimethoxyethane or tetrahydrofuran) in the presence or absence of water, or an aromatic hydrocarbon (eg benzene). The reaction is preferably carried out in the presence of a base such as an alkali or alkaline earth metal carbonate (eg sodium carbonate) at a suitable temperature up to reflux.

Compounds of general formula (I) in which $R^2$, $R^4$ and $R^5$ have a particular meaning may be converted into another compound of the invention by standard methods of interconversion.

For instance, when $R^2$ contains a hydroxy or alkoxy group and/or when $R^4$ and/or $R^5$ represents hydroxy or alkoxy these groups may be interchanged by standard methods of O-alkylation or O-dealkylation. Thus, for example, a compound in which $R^4$ represents hydroxy may be prepared by treating a corresponding compound in which $R^4$ represents methoxy with a reagent system capable of removing the methyl group e.g. a mercaptide such as sodium ethylmercaptide in a solvent such as dimethylformamide, lithium iodide in collidine, boron tribromide in a halohydrocarbon solvent e.g. methylene chloride or molten pyridine hydrochloride.

When $R^2$ contains a hydroxymethyl group this may be converted by oxidation into a corresponding compound of general formula (I) in which $R^2$ contains a group COR$^6$ (where R$^6$ is a hydrogen atom) or CO$_2$H. Thus, for example, oxidation may be effected using a suitable oxidising agent such as a manganese oxidising agent (eg manganese dioxide) in a solvent such as an ether (eg 1,4-dioxan) at a suitable temperature up to reflux, a chromium oxidising agent (eg Jones reagent) or pyridinium dichromate in a suitable solvent such as a halohydrocarbon (e.g. methylene chloride).

When $R^2$ contains an aldehyde group this may be converted by oxidation into a corresponding compound of general formula (I) in which $R^2$ contains a group CO$_2$H. Thus, for example, oxidation may be effected using a suitable oxidising agent such as a source of silver (I) ions (e.g. silver nitrate) in aqueous alkali optionally in the presence of a cosolvent such as an alcohol (e.g. methanol).

Intermediates of formula (II) may be prepared from the corresponding compound of formula (X)

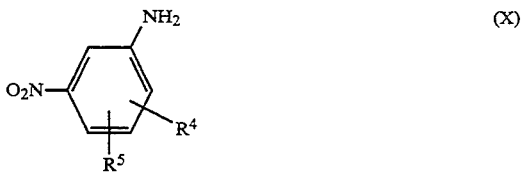

by reaction with a compound of formula (XI)

in the presence of acetic anhydride, followed by reduction of the diketopiperazine intermediate thus formed using for example, borane. The reaction may be carried out at a temperature between 50° C. and reflux, and optionally in a solvent such as an ether, e.g. tetrahydrofuran, or toluene. The nitro group may be subsequently converted into an amine using standard methodology.

Alternatively, intermediates of formula (II) in which $R^4$ is adjacent to $R^3$, and $R^5$ is a hydrogen atom, may be prepared by nitration of a compound of formula (XII)

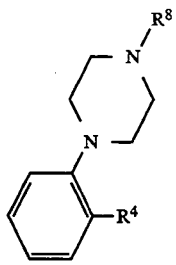

using an appropriate nitrating system such as sulphuric acid and potassium nitrate, or nitronium tetrafluoroborate, in the presence of a solvent, for example, acetonitrile, or alternatively, where $R^8$ is not a hydrogen atom, by nitrosation using, for example, sodium nitrite and a suitable acid such as sulphuric acid in solvent, for example, water, followed in each case by reduction of the nitro or nitroso group using standard methodology.

Intermediates of formula (IV) may be prepared by reduction of the corresponding nitro compound of general formula (XIII)

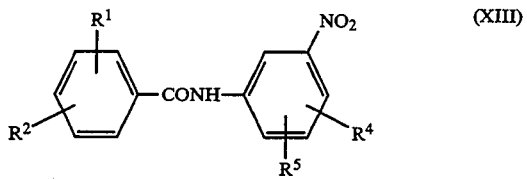

The reduction may be effected by catalytic hydrogenation using a metal catalyst such as palladium or platinum or oxides thereof, preferably, in a solvent such as an alcohol e.g ethanol, or alternatively by using Raney nickel and hydrazine in a solvent such as an alcohol e.g. ethanol.

Intermediates of formula (XIII) may be prepared by condensing a compound of formula (VI) with a compound of formula (X) under the conditions of general process (3).

It will be appreciated that, where necessary, a halogen substituent may be converted into a carboxyl group using standard methodology thus, for example, intermediates of formula (VII) may be prepared from an intermediate of formula (III) by lithiation with, for example, n-butyl lithium followed by quenching with carbon dioxide.

Intermediates of formula (VIIIa) and (VIIIb) may be prepared by reaction of a compound of formula (II) with a compound of formula (XIVa) or (XIVb), respectively,

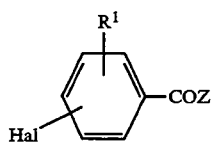

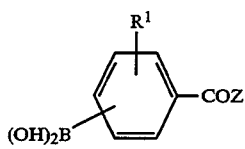

according to the method of general process (3).

The boronic acid intermediates of formulae (VIIIb), (IXa) and (XIVb) or their esters or anhydrides may be used in situ under the conditions described above for general process (4).

Intermediates of formula (VII) may be prepared by the reaction of a compound of formula (IXa) or (IXb) with a compound of formula (XIVa) or (XIVb), respectively, according to the method of general process (4).

Intermediates of formula (II) may also be prepared from the corresponding carboxylic acid using conventional procedures (e.g. by Curtius rearrangement).

Intermediates of formulae (V), (X), (XI), (XII), (XIVa) and (XIVb) are either known compounds or may be prepared by standard methodology or methods analogous to those described herein.

Physiologically acceptable acid addition salts of the compounds of formula (I) may be prepared by treating the corresponding free base with a suitable acid using conventional methods. Thus, for example, a generally convenient method of forming the acid addition salts is to mix appropriate quantities of the free base and the acid in an appropriate solvent eg n alcohol such as ethanol or an ester such as ethyl acetate.

Inorganic basic salts of compounds of formula (i) may be prepared by treating the corresponding acid of formula (I) (i.e. a compound of formula (I) in which $R^2$ contains a group $CO_2H$) with a suitable base using conventional methods.

Salts of compounds of formula (I) may also be converted to different physiologically acceptable salts of compounds of formula (I) using conventional methods.

The invention is illustrated but not limited by the following examples in which temperatures are in °C. Thin layer chromatography (t.l.c.) was carried out on silica plates.

The following abbreviations are used: DMF—dimethylformamide; TEA—triethylamine; HMPA—hexamethylphosphoramide; DME—1,2-dimethoxyethane; THF—tetrahydrofuran; MSC—methanesulphonyl chloride; BTPC—bis(triphenylphosphine)palladium (II) chloride; DMA—dimethylamine; SPC—Short path chromatography carried out on silica (Merck 7747) unless otherwise stated. FCC—Flash column chromatography carried out on silica (Merck 9385). 'Dried' refers to drying using sodium sulphate or magnesium sulphate unless otherwise stated.

The following solvent systems are used: System A—dichloromethane:ethanol:0.88 ammonia; System B—dichloromethane:methanol:0.88 ammonia.

INTERMEDIATE 1

Methyl 4-methoxy-3-(4-methyl-1-piperazinyl)benzoate hydrochloride

A suspension of 2-chloro-N-(2-chloroethyl)-N-methylethanamine hydrochloride (1.92 g) and methyl 3-amino-4-methoxybenzoate (1.81 g) in n-butanol was refluxed with stirring for 19 h. Anhydrous sodium carbonate (0.54 g) was added and refluxing continued for 8.5 h. The solvent was then removed to give an oil which was taken up in water (50 ml) and 2N hydrochloric acid (50 ml) and extracted with ethyl acetate (2×50 ml) The acid solution was then basified with sodium bicarbonate and re-extracted with ethyl acetate (3×50 ml). The extracts were dried and concentrated to a semi-solid (2.47 g) which was absorbed from System A (200:8:1) (5 ml) onto Kieselge G (100 g). Elution with the same solvent gave starting material and minor basic impurities. Further elution with System A (100:8:1) (450 ml) gave first minor impurities and later fractions afforded the free base of the desired product as a gum (0.48 g). This was taken up in methanol (5 ml), filtered and treated with ethereal hydrogen chloride and diluted to 25 ml with ethyl acetate. A cream coloured solid separated and was collected giving the title compound (0.586 g), m.p. 190°–194°. Recrystallisation from methanol:ethyl acetate afforded a sample for analysis.

Analysis Found: C,55.7; H,7.2; N,9.2; Cl, 12.0; $C_{14}H_2ON_2O_3 \cdot HCl$ requires C,55.9; H,7.0; N,9.3; Cl,11.8%

INTERMEDIATE 2

4-Bromo-N-[(2-methoxy-5-nitro)phenyl]benzamide

To a stirred solution of 2-methoxy-5-nitrobenzenamine (1 g) and 4-bromobenzoyl chloride (1.31 g) in THF (5 ml), was added sodium hydroxide (476 mg) in water (5 ml). The mixture was stirred at room temperature for 1.5h. Further THF (5 ml) was added and stirring continued for 1 h. The yellow precipitate was collected by filtration and triturated from ether (30 ml) to give the title compound as yellow solid (1.34 g).

T.l.c. System A (350:8:1), Rf 0.65.

INTERMEDIATE 3

N-[(5-Amino-2-methoxy)phenyl]-4-bromobenzamide

Intermediate 2 (12.6 g) was dissolved in THF (400 ml) and hydrogenated at room temperature over 5% Rhodium on carbon (2.5 g) for 14h. The catalyst was removed by filtration and washed with THF (500 ml). The solvent was evaporated in vacuo to give the title compound as a brown crystalline solid (9.19 g).

T.l.c System A (350:8:1),Rf 0.21

INTERMEDIATE 4

4-Bromo-N-[(2-methoxy-5-(4-methyl-1-piperazinyl)-phenyl]benzamide

A suspension of Intermediate 3 (2 g) and 2-chloro-N-(2- chloroethyl)-N-methylethanamine hydrochloride (1,539 g) in butan-1-ol (30 ml) was heated at reflux, under nitrogen for 18h. Anhydrous sodium carbonate (3.66 g) was added and refluxing continued for a further 24 h. The butanol was evaporated in vacuo to give a brown oil (7.6 g). To this water (75 ml) was added and the solution extracted with ethyl acetate (3×75 ml). The dried extracts were evaporated in vacuo to give a brown oil. This was chromatographed on silica (Merck 7729, 160 g) eluting with System A (250:8:1) to give the title compound as a pink solid (825 mg), m.p. 116.5°–117.5° C.

INTERMEDIATE 5

4-Methoxy-3-(4-methyl-1-piperazinyl)benzoic acid hydrazide

The free base of Intermediate 1 (2 g) in methanol (20 ml) was treated with hydrazine hydrate (4 ml) and refluxed under nitrogen for 16 h. The solution was evaporated and the residue then adsorbed from ethanol onto silica gel [Merck Art. 7734, 5 g]. Purification by SPC eluting with System A (91:9:0 9) gave the title compound as an off-white solid (0.764 g).

T.l.c. System A (90:10:0.1), Rf 0.2.

INTERMEDIATE 6

4-Methoxy-3-(4-methyl-1-piperazinyl)benzenamine

A solution of Intermediate 5 (0.73 g) in water (30 ml) was mixed with concentrated hydrochloric acid (0.6 ml), the solution cooled to 0° to 5° C. and a solution of sodium nitrite (0.219 g) in water (10 ml) added during 5 min. The solution was stirred at 0°–5° C. for 20 min, then 1 h at 23° C., and treated with concentrated hydrochloric acid (40 ml) and acetic acid (40 ml). The mixture was heated at reflux for 2 h, cooled and poured into aqueous sodium hydroxide (5N; 260 ml). The mixture was extracted with ethyl acetate (3×500 ml), and the combined, dried organic extracts were evaporated to give the title compound as a gum (0,190 g).

T.l.c. System A (95:5:0.5) Rf 0.2.

Intermediate 6 was also made by the alternative two-step reaction as follows:

a) 1-Methyl-4-(2-methoxy-5-nitrophenyl)piperazine 1-(2-Methoxyphenyl)-4-methylpiperazine (5.36 g) was acidified with 5N sulphuric acid and the excess water evaporated in vacuo. Concentrated sulphuric acid (95–98%, 22 ml) was added and the mixture stirred at room temperature until homogeneous. To the stirred, dark solution was added portionwise at room temperature potassium-nitrate (3.07 g) in ten portions at intervals of approximately 5 min. The mixture was stirred at room temperature for 4 h then poured onto ice (−500 ml) and the mixture made slightly alkaline with anhydrous sodium carbonate. The basic mixture was extracted with ethyl acetate (4×150 ml) and the combined extracts dried. After 1 h the mixture was filtered and the filtrate evaporated to dryness in vacuo. The dark red residue was diluted with ether (200 ml) and the solid which separated (0.51 g) was filtered off and discarded. The filtrate was evaporated to dryness and the oily residue mixed with ether (300 ml) and the suspension filtered. The fiitrate was evaporated to dryness to give a red gum which very slowly solidified to give the title compound (5.45 g)

T.l.c System A (150:8:1), Rf 0.45

(b) 4-Methoxy-3-(4-methyl-1-piperazinyl)benzeneamine

To a solution of the product of step (a) (5.07 g) in ethanol (70 ml) was added a paste of Raney Nickel in water (2 g). To the warmed suspension was added, with constant agitation, hydrazine hydrate (5 ml) dropwise during 20 min with occasional warming. After the main effervescence had ceased, the suspension was heated for 15 min and then filtered with the aid of ethanol under nitrogen. The residues were kept moist and washed with ethanol and the combined filtrate and washings were evaporated to dryness with the aid of ethanol. The dark residue was re-evaporated with ethanol (20 ml), resuspended in ether (40 ml) and the mixture filtered. The residue was washed with ether and dried to give a solid consisting of the title compound (2,365 g)

T.l.c System A (70:8:1), Rf 0.25.

A further yield of the title compound (0.58 g) was recovered from the ether filtrates and had t.l.c. (as above) Rf 0.25.

INTERMEDIATE 7

4-Bromo-N-[4-methoxy-3-(4-methyl-1-piperazinyl)-phenyl]benzamide

A solution of Intermediate 6 (0.168 g) in pyridine (3 ml) was treated with 4-bromobenzoyl chloride (0.25 g) and stirred at 110°, under nitrogen, for 5 h. Sodium bicarbonate (20 ml; 8%) was added and the mixture was evaporated. The residue was pre-adsorbed onto silica gel [Merck Art. 7734 ca. 5 g] and purified by SPC eluting with System A (97:3:0.3) to give the title compound as a beige solid (0.237 g), m.p. 158.5°–159.5° C.

INTERMEDIATE 8

4-Iodo-2-methoxy-N-[4-methoxy-3-(4-methyl-1-piperazinyl)phenyl]benzamide

A mixture of 4-iodo-2-methoxybenzoic acid (750 mg) and thionyl chloride (7 ml) was stirred at reflux for 15min and then evaporated to give 4-iodo-2-methoxybenzoyl chloride. A solution of Intermediate 6 (629 mg) in THF (30 ml) was treated with a solution of sodium hydroxide (227 mg) in water (10 ml), followed by the 4-iodo-2-methoxybenzoyl chloride, and the mixture stirred at 23° under nitrogen for 24 h. 5M-Hydrochloric acid (1.5 ml) was added, followed by aqueous saturated sodium bicarbonate (10 ml), and the mixture evaporated. The residue was treated with water (50 ml), extracted with ethyl acetate (10×100 ml), and the combined, dried organic extracts were evaporated. The residue was adsorbed from hot ethanol (ca. 40 ml) onto silica gel (Merck 7734, 10 ml), and purified by FCC eluting with System A (945:50:5) to give a solid (780 mg). Crystallisation from ethanol (10 ml) gave the impure title compound, a portion of which (102 mg) was recrystallised from ethanol to give the pure title compound as fine white crystals (37 mg), m.p. 168°–170°.

INTERMEDIATE 9

4-Bromo-N-[4-hydroxy-3-(4-methyl-1-piperazinyl)phenyl]benzamide

A mixture of Intermediate 7 (0.5 g) and pyridine hydrochloride (173 mg) was heated at 180°–200° for 2 h. A further quantity of pyridine hydrochloride (600 mg) was added and the mixture was heated at 180°–200° for 16 h. The resulting residue was mixed with aqueous sodium carbonate (2N;20 ml) and extracted with dichloromethane (3×20 ml). The dried extract was evaporated and the residue was purified on a column of silica eluting with System B (240:10:1) to give the title compound as a white foam (150 mg)

T.l.c System B (240:10:1), Rf 0.3

INTERMEDIATE 10

4-Methyl-3-pyridinylboronic acid

A solution of 3-bromo-4-methylpyridine (5.96 g) in ether (20 ml) was added dropwise to n-butyl lithium in hexane (1.57M;22 ml) in ether (100 ml) at −78° under nitrogen. After 10 min stirring at −78° triisopropylborate (10.2 ml) was added during 2 min. The mixture was stirred at −78° for 30min and allowed to warm to room temperature during 2 h. Water (30 ml) was added and the organic layer was extracted with aqueous sodium hydroxide (0.5N; 33 ml). The combined aqueous layers were washed with ether (30 ml) and then acidified to pH6 with hydrochloric acid (2N). The mixture was stirred until the resulting gum had solidified. Filtration gave the title compound as a white solid (1.5 g).

n.m.r. (CH$_3$OD) δ2.72 (3H,s), 7.88 (1H,brd), 8.58 (1H,brd), 8.69 (1H,brs).

INTERMEDIATE 11

4-Bromo-N-[4-methoxy-3-(4-methyl-1-piperazinyl)phenyl]-3-methylbenzamide

4-Bromo-3-methylbenzoic acid (4.86 g) in an excess of thionyl chloride (25 ml) was heated to reflux for 1 h. The excess thionyl chloride was then evaporated and the acid chloride then added to a mixture of a solution of Intermediate 6 (5.0 g) in THF (25 ml) and sodium hydroxide (1.8 g) in water (30 ml). The resulting solution was then stirred at room temperature, under nitrogen, overnight. The solvent was removed by evaporation, water (40 ml) added and the mixture extracted with dichloromethane (5×50 ml). The extracts were dried and evaporated to give a brown/orange sticky foam. This was purified by FCC eluting with System B (970:20:10) to give the title compound (5.73 g).

T.l.c. System B (970:20:10) Rf=0.11

INTERMEDIATE 12

3,4-Dimethoxy-5-nitrobenzoic acid

To a solution of potassium permanganate (3.05 g) in water (100 ml) was added to a solution of 3,4-dimethoxy-5-nitrobenzaldehyde (2.7 g) in acetone (80 ml). The mixture was then stirred at 20° for 18h whereupon the acetone was evaporated and the residue acidified (2N HCl) and was then decolourised by the addition of sodium metabisulphite sodium. The mixture was then extracted with ethyl acetate (3×200 ml) and the dried extracts evaporated to give the title compound as a colourless solid (2.08 g) m.p. 197°–198°.

INTERMEDIATE 13

Methyl 3,4-dimethoxy-5-nitrobenzoate

Intermediate 12 (1 g) was dissolved in methanol:conc. sulphuric acid (9:1; 20 ml) and was stirred at 20° for 2 h, and was then heated to reflux for 2 h. The cooled mixture was added to 8% NaHCO$_3$ solution (50 ml). The methanol was then evaporated and the residue extracted with ethyl acetate (2×75 ml). The dried extracts were evaporated to give the title compound as a cream solid (1 g), m.p. 75°–76°.

INTERMEDIATE 14

Methyl 3-amino-4,5-dimethoxybenzoate

A solution of Intermediate 13 (990 mg) in ethanol (15 ml) was hydrogenated over 10% palladium on carbon for about 5 h. The mixture was filtered and was evaporated to give a pale pink oil which crystallised to give the title compound (883 mg).

T.l.c ethyl acetate:hexane (1:2) Rf 0.15.

INTERMEDIATE 15

Methyl 3,4-dimethoxy-5-(4-methyl-1-piperazinyl)benzoate

A mixture of Intermediate 14 (1.9 g), 2-chloro-N-(2-chloroethyl)-N-methylethanamine hydrochloride (1.73 g) and sodium carbonate (3.81 g) in 3-methyl-3-pentanol (70 ml) was heated to reflux for 42 h. The solvent was evaporated and the residue partitioned between water (100 ml) and ethyl acetate (2×100 ml). The dried ethyl acetate extracts were evaporated to give a pale yellow oil (2.2 g). This material was chromatographed eluting with System A (200:8:1) to give the title compound as a pale yellow oil which crystallised on standing (369 mg).

T.l.c. System A (200:8:1) Rf 0.3

INTERMEDIATE 16

3,4-Dimethoxy-5-(4-methyl-1-piperazinyl)benzoic acid hydrazide

Intermediate 15 (651 mg) was dissolved in methanol (15 ml) containing hydrazine hydrate (2 ml) and was heated to reflux for 18 h. The cooled mixture was evaporated and the residue partitioned between water (30 ml) and dichloromethane (2×30 ml). The dried dichloromethane extracts were evaporated to give the title compound as a colourless solid (520 mg)T.l.c. System A (100:8:1) Rf 0.20

INTERMEDIATE 17

3,4-Dimethoxy-5-(4-methyl-1-piperazinyl)benzenamine

Intermediate 16 (510 mg) in water (5 ml) was treated with conc. HCl (5 ml), cooled (0°), and a solution of sodium nitrite (144 mg) in water (2 ml) added over 5 min. Stirring was continued at 0° for 20 min, then at 20° for 1 h. Conc. HCl (5 ml) and glacial acetic acid (5 ml) were then added, and the mixture heated to reflux for 2 h. The cooled mixture was poured into 2N NaOH (100 ml) and was then extracted with ethyl acetate (2×100 ml). The dried extracts were evaporated to give a brown oil. This was chromatographed eluting with System A (100:8:1) to give the title compound as a red-brown oil which crystallised (139 mg).
T.l.c. System A (100:8:1) Rf 0.20

INTERMEDIATE 18

4-Bromo-N-[3,4-dimethoxy-5-(4-methyl-1-piperazinyl)-phenyl]benzamide

A mixture of Intermediate 17 (134 mg) and 4-bromobenzoyl chloride (117 mg) in THF (8 ml) and water (4 ml) was stirred at 20° for 3 h in the presence of sodium hydroxide (42 mg). The THF was evaporated and the residue was partitioned between water (25 ml) and dichloromethane (2×50 ml). The dried extracts were evaporated to give an off-white foam (240 mg) which was chromatographed eluting with System A (200:8:1) to give the title compound as an off-white foam (210 mg).
T.l.c System A (100:8:1) Rf 0.43.

INTERMEDIATE 19

1-(2-Methoxy-5-nitrophenyl)piperazine

Potassium nitrate (6.06 g) was added portionwise during 2 h to a solution of 1-(2-methoxyphenyl)piperazine ( 10.0 g) in sulphuric acid (50 ml; 95%) at room temperature. The resulting brown solution was stirred at room temperature for 30 min and added cautiously to ice (300 ml). The solution was basified with aqueous sodium hydroxide (5N) and extracted with ethyl acetate (2×400 ml). The dried extract was evaporated and the residue was purified on a column of silica (190:10:1) to give the title compound as a yellow solid (9.4 g). m.p. 102°-104° C.

INTERMEDIATE 20

4-Methoxy-3-(1-piperazinyl)benzeneamine

A solution of Intermediate 19 (9.3 g) in ethanol (100 ml) was hydrogenated over 10% palladium on charcoal (1 g) for 3 h. The suspension was filtered and evaporated and the residue was purified on a column of silica eluting with System B (90:10:1) to give the title compound as a brown foam (7.5 g).

T.l.c. System B (90:10:1),Rf 0.15.

INTERMEDIATE 21

1,1-Dimethylethyl 4-(5-amino-2-methoxyphenyl)-1-piperazinecarboxylate

A solution of di-tert butyl dicarbonate (3.3 g) in dichloromethane (10 ml) was added dropwise to a suspension of Intermediate 20 (3.0 g) in TEA ( 4 ml ) and dichloromethane ( 20 ml ) . The resulting solution was stirred for 2h and treated with aqueous sodium carbonate (2N; 50 ml). The mixture was extracted with dichloromethane (3×50 ml) and the dried extract was evaporated to give a yellow foam which was purified on a column of silica eluting with System B (240:10:1) to give the title compound as a yellow foam (1.9 g).
T.l.c. System B (90:10:1), Rf 0.7.

INTERMEDIATE 22

1,1-Dimethylethyl 4-[5-[(4-bromobenzoyl)amino]-2-methoxyphenyl]-1-piperazinecarboxylate A solution of 4-bromobenzoyl chloride (770 mg) in THF (2 ml) was added in one portion to a mixture of Intermediate 21 (1.0 g), sodium hydroxide (200 mg), water (10 ml), and THF (10 ml). The mixture was stirred for 30 min, diluted with water (50 ml) and extracted with dichloromethane (3×50 ml). The dried extract was evaporated and the residue was purified on a column of silica eluting with ether to give the title compound as a white solid (1.6 g), m.p. 156°-158°.

INTERMEDIATE 23

1,1-Dimethylethyl 4-[[2-methoxy-5-[4-(4-pyridinyl)benzoyl]amino]phenyl]-1-piperazinecarboxylate A mixture of Intermediate 22 (1.0 g), 4-pyridineboronic acid (250 mg) tetrakis(triphenylphosphine)palladium (0) (50 mg), DME (20 ml), and aqueous sodium carbonate (2N;4mmol) was refluxed under nitrogen for 2 h. The mixture was treated with water (50 ml) and extracted with dichloromethane (3×50 ml). The dried extract was evaporated and the residue was purified on a column of silica eluting with ethyl acetate to give the title compound as a white solid (750 mg) mp 229°-230°.

INTERMEDIATE 24

2-Fluoro-4-iodobenzoic acid

2-Fluoro-4-iodo-1-methylbenzene (1.0 g) was added to a solution of potassium permanganate (2.0 g) in water (25 ml). The mixture was gently refluxed for 2 h. Tetrabutylammonium bisulphate (100 mg) was added and the mixture was refluxed for 18h. The cooled solution was treated with ethyl acetate (100 ml) and water (50 ml) and the brown suspension was filtered. The dried organic phase was evaporated and the resulting solid was partitioned between aqueous sodium bicarbonate (2N; 50 ml) and diethyl ether (2×30 ml). The basic solution was acidified with hydrochloric acid (2N) and extracted with dichloromethane (3×50 ml). The dried extract was evaporated to give the title compound as a white solid (120 mg), m.p. 158°-159°.

INTERMEDIATE 25

4-Bromo-N-[4-methoxy-3-(4-methyl-1-piperazinyl)-phenyl]-2-methylbenzamide

A suspension of 4-bromo-2-methylbenzoic acid (706 mg) in thionyl chloride (3 ml) was refluxed under nitrogen for 3 h and evaporated. The residual acid chloride was dissolved in THF (5 ml) and added in one portion to a solution of Intermediate 6 (500 mg) and sodium hydroxide (240 mg) in THF (10 ml) and water (5 ml). The solution was stirred for 20 min, diluted with water (50 ml), and extracted with dichloromethane (3×50 ml). The dried extract was evaporated and the residue was purified on a column of silica (Merck 9385) eluted with system B (485:15:1.5) to give the title compound as a yellow foam (630 mg).

T.l.c. System B (240:10:1), Rf 0.3.

Similarly prepared was:

INTERMEDIATE 26

2-Fluoro-4-iodo-N-[4-methoxy-3-(4-methyl-piperazinyl) phenyl]benzamide as a yellow foam (870 mg)

T.l.c. System B (240:10:1) Rf=0.3

From a suspension of Intermediate 24 (800 mg) in thionyl chloride (4 ml), added in one portion to a solution of Intermediate 6 (663 mg) in THF (20 ml) and aqueous sodium hydroxide (2N; 6 ml).

INTERMEDIATE 27

1-(2-Methyl-5-nitrophenyl)-4-methyl-2,6-piperazinedione

A suspension of N-methyliminodiacetic acid (2.00 g) in acetic anhydride (10 ml) was stirred at room temperature for 10 min and then heated to 150° C. for 1 h, after which time the solution had turned dark brown. The solution was concentrated in vacuo and about 10 ml of distillate was collected. The resulting brown gum was then treated with 2-methyl-5-nitrobenzenamine (2.06 g) suspended in toluene (20 ml). The resulting mixture was heated to 100° C. for 60 min before allowing to cool overnight, giving a precipitate which was collected by filtration, washed with cold toluene (3×10 ml) and then air-dried for 2 min. The solid was then added to a flask containing acetic anhydride (15 ml) and heated to 140° C. for 20 min. The mixture was then allowed to cool to 60° C. before being concentrated in vacuo to give 10 ml of distillate. The crystalline solid which was formed as the residue cooled was filtered off, washed with ether then recrystallised from methanol (20 ml) to give the title compound as crystalline brown solid (1.78 g). m.p. 157°–158° C.

INTERMEDIATE 28

4-Methyl-1-(3-nitrophenyl)piperazine

A solution of 1-(3-nitrophenyl)piperazine hydrochloride (1.80 g) in water (7 ml) was basified with anhydrous sodium carbonate (0.8 g) and the mixture evaporated to dryness in vacuo. The solid was mixed with formic acid (17 ml) and a solution of formaldehyde 36% in water (1.3 ml, ≡0.47 g CH$_2$O) added and the mixture heated at 95°–98° for 3 h. The mixture was diluted with water (35 ml) and basified with anhydrous sodium carbonate. The suspension was extracted with ethyl acetate (2×80 ml) and the extract dried for 1 h. The mixture was filtered and the filtrate evaporated to dryness to give a dark red oil which was dissolved in ether (20 ml) and filtered. The filtrate was evaporated to dryness to give a red oil which was purified by FCC eluting with System A (500:8:1) to give an orange oil which was dried in vacuo. Upon scratching, crystallisation began and the oil was left to stand until crystallisation of the title compound was complete (1.10 g) m.p. 53°–54° C.

INTERMEDIATE 29

1-(5-Amino-2-methylphenyl)-4-methyl-2,6-piperazinedione

A suspension of Intermediate 27 (1.70 g) in ethanol:water (5:2, 50 ml) was added under vacuum to a suspension of 10% palladium on charcoal 50% paste (600 mg) in ethanol:water (5:2, 20 ml). The resulting suspension was stirred at room temperature under an atmosphere of hydrogen until uptake ceased. The suspension was filtered, concentrated in vacuo, and the residue was dissolved in dichloromethane, dried, filtered and concentrated in vacuo to give the title compound as a cream coloured foam (1.51 g) which was dried in vacuo.

T.l.c. System A (150:8:1), Rf=0.41.

Similarly prepared was:

INTERMEDIATE 30

3-(4-Methyl-1-piperazinyl)benzeneamine as a pale orange oil which crystallised after scratching and was dried in vacuo (0.904 g), m.p. 75°–76° C.

From a suspension of Intermediate 28 (1.10 g) in ethanol:water (5:2, 20 ml).

INTERMEDIATE 31

4-Methyl-3-(4-methyl)piperazinyl)benzenamine

A solution of Intermediate 29 (1.48 g) in dry THF (60 ml) at reflux under nitrogen, was treated dropwise with borane-THF complex (1 molar solution, 25.5 ml). The resulting mixture was heated at reflux under nitrogen for 22h before cooling and treating with 2N hydrochloric acid (10 ml) very slowly. The mixture was then heated to reflux for a further 2h before cooling to room temperature and concentrating in vacuo to a volume of about 10 ml. The residue was diluted with 2N sodium carbonate (100 ml) and extracted with ethyl acetate (3×100 ml). The combined, dried extracts were concentrated in vacuo and purified by FCC eluting with System A (150:8:1) to give the title compound as a crystalline pale yellow solid (922 mg) m.p. 83°–84° C.

INTERMEDIATE 32

4-Bromo-N-[4-methyl-3,-(4-methyl-1-piperazinyl)-phenyl]benzamide

A solution of 4-bromobenzoyl chloride (1.469 g) in THF (5 ml) was added to a stirred solution of Intermediate 31 (915 mg) in THF (15 ml) and water (10 ml) containing sodium hydroxide (350 mg). The mixture was stirred at room temperature under nitrogen for 2½h before adding water (50 ml) and extracting with dichloromethane (3×50 ml) The combined extracts were dried and concentrated in vacuo to give a pale yellow foam. The foam was dissolved in dichloromethane (5 ml) to give a yellow solution which solidified. Excess dichloromethane was removed in vacuo and ether was added (25 ml). The solid was triturated and then filtered, and dried in vacuo at 60° C. for 2 h to give the title compound as an off-white solid (1.46 g) m.p. 208°–209° C.

Similarly prepared was:

INTERMEDIATE 33

4-Bromo-N-[3-(4-methyl-1-piperazinyl)phenyl]benzamide as a white solid (1.53 g) m.p. 167°–168° C.

From a solution of 4-bromobenzoyl chloride (1.174 g) in THF (4 ml) and a stirred solution of Intermediate 30 (0.90 g) in THF (15 ml) and water (10 ml) containing sodium hydroxide (380 mg). Purification by FCC eluting with System A (350:8:1) gave the title compound.

INTERMEDIATE 34

2-Methoxy-3-(4-methyl-1-piperazinyl)benzoic acid 1-(2-Methoxyphenyl)-4-methylpiperazine (10.0 g) was added in ether (20 ml) dropwise to a solution of n-butyllithium in hexane (1.6M; 36 ml) and N,N-tetramethylethylenediamine (5.6 g) under nitrogen at room temperature. The resulting suspension was stirred for 6 h and was added slowly to a mixture of solid carbon dioxide (50 g) and THF (50 ml). The mixture was allowed to warm to room temperature and was treated with water (150 ml). The aqueous solution was washed with and the filtrate was evaporated to give the title compound as a ether (2×200 ml), acidified with hydrochloric acid (2N) and evaporated. The solid was treated with methanol (150 ml), filtered white solid (15.0 g)

n.m.r. ($D_2O$) δ3.04 and 3.0–3.15 (7H, m +s), 3.38 (2H, br.m), 3.65 (2H, br.d), 3.9 (3H, s), 7.15–7.35 (3H, m).

INTERMEDIATE 35

Phenylmethyl [2-methoxy-3-(4-methyl-1-piperazinyl)phenyl]carbamate

Intermediate 34 (5 g) was suspended in thionyl chloride (50 ml) and refluxed for 3 h under nitrogen. The excess thionyl chloride was removed by evaporation and the resulting solid was suspended in acetone (150 ml). A solution of sodium azide (2.34 g) in water (25 ml) was added dropwise and the mixture was stirred for 2 h. The solution was neutralised and was extracted with dichloromethane (3×100 ml). The extract was washed with hydrochloric acid (2N; 100 ml) and the acid phase was basified with aqueous sodium carbonate (2N) and extracted with dichloromethane (3×50 ml). This extract was dried, evaporated and the residue was purified on a column of silica (Merck 9385) eluted with System B (485:15:1.5) to give the title compound as a brown gum (90 mg).

T.l.c. System B (90:10:1), Rf 0.6.

INTERMEDIATE 36

2-Methoxy-3-(4-methyl-1-piperazinyl)benzenamine

A solution of Intermediate 35 (50 mg) in benzyl alcohol (10 ml) was treated with aqueous sodium hydroxide (5N; 2 ml) and heated at gentle reflux for 4 h. The solution was diluted with water (50 ml) and extracted with dichloromethane (3×50 ml). The dried extract was evaporated to give a benzyl alcohol phase. The benzyl alcohol solution was applied to a column silica (Merck 9385) eluted with ethyl acetate followed by ethyl acetate:methanol:ammonia (90:10:1) to give the title compound as a yellow gum (80 mg).

T.l.c. System B (90:10:1) Rf 0.7

INTERMEDIATE 37

4-Bromo-N-[2-methoxy-3-(4-methyl-1-piperazinyl)phenyl]benzamide

A solution of 4-bromobenzoyl chloride (150 mg) in THF (1 ml) was added in one portion to a solution of Intermediate 36 (120 mg) and sodium hydroxide (40 mg) in THF (3 ml) and water (2 ml). The mixture was stirred for 30 min and was treated with a further sample (150 mg) of 4-bromobenzoyl chloride. The mixture was stirred for 1 h, diluted with water (20 ml) and extracted with dichloromethane (3×50 ml). The dried extract was evaporated to give an orange solid which was triturated with ether (1 ml) to give a yellow solid. The solid was purified on a column of silica (Merck 9385) eluted with System B (240:10:1) to give the title compound as a white solid (50 mg).

T.l.c System B (90:10:1) Rf=0.8.

INTERMEDIATE 38

3-Methoxy. 4-[(trifluoromethylsulphonyl)oxy]benzoic acid

Trifluoromethanesulphonic anhydride (10.0 g, 6 ml) in dry dichloromethane (50 ml) was added dropwise to a stirred solution of 4-hydroxy-3-methoxybenzoic acid (4.0 g) in dry dichloromethane (50 ml) and pyridine (dry, 3.3 ml) at 0° C. under nitrogen. The reaction mixture was stirred at 0° C. for a further 2 h, sodium bicarbonate (8% solution) was added until basic and then the reaction mixture was extracted with ether (4×50 ml). Acidification of the evaporated ether residues with hydrochloric acid (2N) and extraction with dichloromethane (4×50 ml) followed by evaporation to dryness gave a gave a yellow/white solid (3.55 g). This was purified by FCC eluting with hexane:ethyl acetate:acetic acid (740:250:10) to give the title compound as an off-white solid (1.43 g) m.p. 120°–122° C.

INTERMEDIATE 39

3-Methoxy-4-(4-pyridinyl)benzoic acid

Intermediate 38 (1.06 g), 4-pyridinylboronic acid (486 mg), DME (25 ml), 2N sodium carbonate (10 ml) and tetrakis(triphenylphosphine) palladium (0) (70 mg), were heated to reflux for 18 h under nitrogen. After allowing to cool to room temperature, water (50 ml) was added and the mixture was washed with ethyl acetate (2×50 ml). The aqueous phase was neutralised with 2N hydrochloric acid, and then concentrated in vacuo onto silica (Merck 9385). Purification by FCC eluting with ethyl acetate:hexane:acetic acid (750:240:10) gave a pale orange solid which was triturated in ether and dried under high vacuum to give the title compound as a pale orange solid (370 mg) m.p. 239°–241° C.

INTERMEDIATE 40

1-(2-Chloro-5-nitrophenyl)-4-methylpiperazine

A mixture of 2-chloro-5-nitrobenzenamine (7.95 g) and 2-chloro-N-(2-chloroethyl)-N-methylethanamine hydrochloride (8.86 g) in chlorobenzene (40 ml) under nitrogen was heated to reflux for 3 days before cooling and diluting with dichloromethane (60 ml). The reaction mixture was then extracted with water (2×500 ml), the aqueous layers combined and basified with 2N sodium hydroxide, then extracted with dichloromethane (4×400 ml). The combined, dried extracts were concentrated in vacuo to give a dark brown oil (7.82 g)

which was purified by FCC eluting with ether to give a dark brown oil which crystallised upon standing. This material was dissolved in ethanol (40 ml) and boiled up with some charcoal (300 mg). The hot ethanolic suspension was filtered through a pad of hyflo and concentrated in vacuo to give the title compound as a yellow oil which crystallised on standing (5.25 g) m.p.63°–64° C.

INTERMEDIATE 41

1-(2-Fluoro-5-nitrophenyl)-4-methylpiperazine

A mixture of 2-fluoro-5-nitrobenzenamine (4.06 g) and 2-chloro-N-(2-chloroethyl)-N-methylethanamine hydrochloride (5.01 g) in chlorobenzene (20 ml) was heated at reflux under nitrogen for 2½ days before cooling to room temperature- The dark tar-like material was dissolved in methanol (150 ml), the solution then concentrated in vacuo with silica and the product purified twice by FCC eluting with System A (400:8:1) followed by System A (300:8:1) to give the title compound as a crystalline brown solid (360 mg).

T.l.c. System A (400:8:1) Rf=0.15

INTERMEDIATE 42

4-Chloro-3-(4-methyl-1-piperazinyl)benzenamine

A solution of Intermediate 40 (5.06 g) in ethanol (60 ml) and water (10 ml) was treated with Raney Nickel (2 g of a slurry in water) under nitrogen. This mixture was cooled to 18° C. and treated dropwise with hydrazine hydrate (4 ml) over 15 minutes. The resultant mixture was stirred at room temperature for 2 hours, filtered and concentrated in vacuo to give an oil which crystallised upon cooling. The pale brown crystalline solid was dried in vacuo to give the title compound as a brown crystalline solid (4.36 g). m.p. 96°–97° C.

INTERMEDIATE 43

4-Fluoro-3-(4-methyl-1-piperazinyl)benzenamine

A solution of Intermediate 41 (350 mg) in ethanol and water (5:2,10 ml) was added under vacuum to a prehydrogenated suspension of 10% palladium on carbon, 50% paste (166 mg) in ethanol and water (5:2, 4 ml). The resulting suspension was stirred at room temperature under an atmosphere of hydrogen for 30 minutes. The suspension was filtered and the filter-cake washed with ethanol and water (5:2,50 ml). The combined filtrates were concentrated in vacuo, the residue dissolved in dichloromethane (20 ml) and dried. The filtered solution was concentrated in vacuo to give the title compound as a buff coloured solid (272 mg). m.p. 155°–156° C.

INTERMEDIATE 44

4-Bromo-N-[4-chloro-3-(4-methyl-1-piperazinyl)-phenyl]benzamide

A solution of Intermediate 42 (500 mg) in dry THF (8 ml) and water (8 ml) containing sodium hydroxide (182 mg), was treated with a solution of 4-bromobenzoyl chloride (730 mg) in dry THF (4 ml). The resulting mixture was stirred at room temperature for 4 hours. The mixture was added to water (50 ml) and extracted with dichloromethane (3×40 ml). The combined, dried extracts were concentrated in vacuo to give a yellow foam which was triturated in dry ether (3×3 ml) and dried in vacuo to give a cream-coloured solid (776 mg). This was dissolved in methanol, concentrated in vacuo onto silica and purified by FCC eluting with System A (300:8:1) to give the title compound as a white solid (619 mg) m.p. 204°–205°

Similarly prepared was:

INTERMEDIATE 45

4-Bromo-N-[4-fluoro-3-(4-methyl-1-piperazinyl)-phenyl]benzamide as a cream-coloured solid (260 mg) m.p. 125°–127° C.

From a solution of Intermediate 43 (245 mg) in dry THF (4 ml) and water (4 ml) containing sodium hydroxide (94 mg), treated with a solution of 4-bromobenzoyl chloride (390 mg) in dry THF (2 ml).

INTERMEDIATE 46

4-(2-Butoxyphenyl)-1-methylpiperazine

A stirred solution of 2-butoxybenzenamine (6.50 g) in chlorobenzene (50 ml) was treated with 2-chloro-N-(2-chloroethyl)-N-methylethanamine hydrochloride (7.70 g) according to the method of Intermediate 40. Concentration in vacuo of the dichloromethane extracts gave the title compound as a red oil (9.67 g).

T.l.c: ether:hexane (5:1), Rf=0.1.

INTERMEDIATE 47

4-(2-Butoxy-5-nitrophenyl)-1-methylpiperazine

Sulphuric acid (95%, 30 ml) was added to Intermediate 46 (9.5 g) and the resulting glassy/gummy mixture was stirred at room temperature until all material had dissolved. The solution was then treated portionwise with potassium nitrate (4.17 g) over 45min at 25° C., and the mixture then stirred for 40min before pouring into ice (80 ml) and basifying with 5N sodium hydroxide. The solution was extracted with ethyl acetate (4×500 ml) and the combined, dried extracts were concentrated in vacuo to give a dark orange oil (6.9 g). Purification by FCC, eluting with ether, gave the title compound as a dark orange oil which crystallised on standing to give a yellow solid (4.597 g), m.p. 72° C.

INTERMEDIATE 48

4-Butoxy-3-(4-methyl-1-piperazinyl)benzenamine

A solution of Intermediate 47 (4.518 g) in ethanol:water (5:2, 50 ml) was added under vacuum to a prehydrogenated suspension of palladium (10% palladium on carbon, 50% paste with water, 0.9 g) in ethanol:water (5:2, 35 ml). The resulting suspension was stirred at room temperature under an atmosphere of hydrogen. The catalyst was filtered off, the pad was washed with ethanol:water (70 ml, 5:2) and the combined filtrates concentrated in vacuo to give a dark orange oil (4.5 g). Purification by FCC eluting with System A (150:8:1) gave the title compound as a dark orange oil (3.88 g).

T.l.c. System A (150:8:1), Rf 0.16.

INTERMEDIATE 49

4-Bromo-N-[4-butoxy-3-(4,methyl-1-piperazinyl)-phenyl]benzamide

A stirred solution of Intermediate 48 (2.00 g) in THF (30 ml) was treated with a solution of sodium hydroxide (610 mg) in water (30 ml) and then 4-bromobenzoyl chloride (2.50 g), according to the method of Intermediate 44. Purification by FCC eluting with System A (200:8:1) gave the title compound as a cream-coloured solid (1.71 g). Concentration of earlier, impure fractions gave a solid which was triturated in ether and dried in vacuo to give a second batch of title compound as a cream-coloured solid (574 mg) m.p. 142°–144° C.

INTERMEDIATE 50

4-Methyl-3-pyridinylboronic acid, methyl ester

A solution of 3-bromo-4-methylpyridine (1 g) in dry ether (30mλ) was added over 8 min (keeping the internal temperature below −72°) to a stirred, cooled (dry ice-acetone) solution of n-butyl lithium (1.69M; 3.6 ml) in dry ether (18 ml) under nitrogen. After a further 10 min, triisopropylborate (1.85 ml) was added over 3 min. After a further 5 min the cooling bath was removed and the mixture allowed to warm to room temperature over 1 h, Water (30 ml) and sodium hydroxide (2N; 3 ml) were added and the aqueous layer washed with ether. The aqueous layer was adjusted to pH6 with 2N hydrochloric acid and then evaporated in vacuo to leave a semi-solid residue, The residue was re-evaporated with ethanol (20 ml) and triturated with ether to give a white solid (1,4 g). A sample (1.1 g) of this solid was dissolved in warm (40°) methanol (17 ml) and the solution filtered and seeded, Filtration gave the title compound (0,24 g) as a white solid.

T.l.c, methanol:triethylamine (95:5) Rf 0,21

INTERMEDIATE 51

2-Hydroxy-4-iodo-N-[4-methoxy-3-(4-methyl-1-piperazinyl) phenyl]benzamide

A suspension of 4-iodosalycylic acid (500 mg) in thionyl chloride (5 ml) was refluxed for 1 h and evaporated, The residue in pyridine (3 ml) was treated with Intermediate 6 (350 mg) and the mixture was stirred at room temperature for 2 h and at reflux for 16 h, The mixture was diluted with dichloromethane (50 ml) and washed with aqueous sodium bicarbonate (1N; 50 ml), The dried organic phase was evaporated and the residue was purified by FCC eluting with system B (240:10:1) to give a yellow gum, The gum was triturated with ether (3 ml) to give the title compound as a yellow powder (280 mg).

T.l.c. System B (90:10:1) Rf 0,45.

INTERMEDIATE 52

Methyl 4-bromo-3-methylbenzoate

4-Bromo-3-methylbenzoic acid (10 g) was suspended in methanol (50 ml) containing conc. sulphuric acid (2 ml). The mixture was heated to reflux for 18 h, On addition of 8% NaHCO$_3$ (100 ml) to the cooled reaction, a flocculent solid was filtered off and dried in vacuo at 40°–45° to give the title compound as a liquid which recrystallised on cooling (10.25 g) m.p. 39.5°–40.5°

INTERMEDIATE 53

Methyl 3-methyl-4-(4-pyridinyl)benzoate

A mixture of Intermediate 52 (736 mg) and sodium carbonate (2N, 3 ml) in DME (8 ml) was treated with 4-pyridinylboronic acid (400 mg) and tetrakis(triphenylphosphine)palladium (0) (25 mg). The mixture was heated to reflux and stirred under nitrogen for 18 hours, before cooling to room temperature and adding to water (20 ml). The mixture was extracted with dichloromethane (3×20 ml) and the combined extracts dried and concentrated in vacuo to give a yellow oil. Purification by FCC eluting with System A (350:8:1) gave the title compound as a yellow oil which slowly recrystallised m.p. 70°–71° C.

INTERMEDIATE 54

[4-[[[4-Methoxy-3-(4-methyl-1-piperazinyl)phenyl]amino]carbonyl]phenyl]boronic acid n-Butyllithium (7.5 ml of 1.6M solution in hexane) was added dropwise at −90° to −100° to a stirred solution of Intermediate 7 (404 mg) and triisopropylborate (2.77 ml) in dry THF (20 ml) over 45min under nitrogen, and stirring continued for 1.5 h at −90° to −103° for 1.5 h. After 3 h at −78°, the cooling bath was removed and the mixture stirred at +23° for 11 h. Water (4 ml) was added, and, after 1 h, the mixture was evaporated. The residue was adsorbed from System A (50:45:5) onto silica gel (Merck 7734, 10 ml) and purified by FCC eluting with System A (89:10:1→50:45:5) to give firstly recovered impure starting material followed by the title compound as a cream foam (280 mg)

T.l.c. System A (50:45:5) Rf 0.04

INTERMEDIATE 55

4-Fluoro-2-methoxybenzenamine

A solution of 5-fluoro-2-nitrophenol (10.0 g) in dry acetone (40 ml) under nitrogen was treated with potassium carbonate (8.9 g). The mixture formed a deep red coloured thick precipitate. Methyl iodide (5 ml, 11.4 g) was added slowly and the mixture stirred overnight and then at 60° C. for 3 hours. Further methyl iodide (3 ml, 6.84 g) was added and the mixture stirred at 60° C. for a further 3 hours. The mixture was added to water (50 ml) and sodium hydroxide (2N, 40 ml), and extracted with dichloromethane (3×100 ml) . The combined, dried extracts were concentrated in vacuo to give a yellow oil which upon cooling crystallised giving a pale yellow crystalline solid (10.88 g). A solution of this solid in ethanol:water (200 ml, 6:2) was added under vacuum to a prehydrogenated suspension of palladium (10% on carbon, 50% paste, 2.5 g) in ethanol:water (80 ml, 6:2). The suspension was stirred under an atmosphere of hydrogen for 2 hours, the suspension was filtered through Hyflo. The combined filtrates were concentrated in vacuo and the moist residue re-evaporated with ethanol. The purple oily residue was dissolved in dichloromethane (200 ml), dried and concentrated in vacuo to give the title compound as a dark purple liquid. (7.73 g).

Analysis: Found: C, 59.8; H, 6.1; N, 9.8 C$_7$H$_8$FNO requires: C,59.6; H, 5.7; N, 9.9%

INTERMEDIATE 56

1-(4-Fluoro-2-methoxyphenyl)-4-methylpiperazine

A mixture of Intermediate 55 (7.70 g) and 2-chloro-N-(2-chloroethyl)-N-methylethanamine hydrochloride (11.7 g) in chlorobenzene (60 ml) was heated to reflux and stirred for 10 hours, then cooled to room temperature, diluted with dichloromethane (100 ml) and extracted with water (3×100 ml). The solution was made slightly acidic with 2N hydrochloric acid, then basic (pHS-9) with 2N sodium hydroxide and extracted with dichloromethane (4×75 ml). The combined, dried extracts were concentrated in vacuo to give a dark brown oily residue. This was purified by FCC eluting with System A (300:8:1) and dried in vacuo to give the title compound as a dark brown oil (1.312 g).

T.l.c. System A (150:8:1) Rf=0.37

INTERMEDIATE 57

1-(4-Fluoro-2-methoxy-5-nitrophenyl)-4-methylpiperazine

Intermediate 56 (1.25 g) was added dropwise to conc. sulphuric acid (4 ml). The mixture was stirred until complete solution of material was effected, and then treated portionwise at 25° with potassium nitrate (0.712 g). The mixture was stirred at room temperature for 2 hours then poured into ice (20 g). The aqueous solution was then neutralised with 0.88 aqueous ammonia and basified (pH5) with 2N sodium carbonate. The mixture was extracted with dichloromethane (4×10 ml) and the combined, dried extracts concentrated in vacuo to give the title compound as a dark orange oil (1,349 g), which crystallised upon standing.

INTERMEDIATE 58

2-Fluoro-4-methoxy-5-(4-methyl-1-piperazinyl)benzenamine

A solution of Intermediate 57 (1.30 g) in ethanol:water (7:2, 45 ml) was added under vacuum to a prehydrogenated suspension of palladium on charcoal (10% Pd on C, 50% paste, 480 mg) in ethanol:water (7:2, 18 ml). The suspension was stirred under an atmosphere of hydrogen for 3 hours and filtered through hyflo. The combined filtrates and washings were evaporated to dryness and the residue dissolved in dichloromethane, dried, filtered and concentrated in vacuo to give the title compound as a purplish/brown solid (1,065 g)

n.m.r. (CDCl$_3$) δ 2.35 (3H,s), 2.60 (4H,m), 3.01 (4H,m), 3.40 (2H,b.rs), 3.79 (3H,s), 6.43 (1H,d), 6.60 (1H,d).

INTERMEDIATE 59

4-Bromo-N-[2-fluoro-4-methoxy-5-(4-methyl-1-piperazinyl)phenyl]-3-methylbenzamide A suspension of 4-bromo-3-methylbenzoic acid (606 mg) in thionyl chloride (3 ml) under nitrogen, was heated to reflux for 2 hours. The solution was evaporated to dryness in vacuo, the oily residue dissolved in THF (5 ml) and the solution added slowly to a stirred solution of Intermediate 58 (657 mg) in THF (30 ml) and 2N sodium hydroxide (3 ml). The mixture was stirred at room temperature for 4 hours, before pouring into water (100 ml) and extracting with dichloromethane (3×100 ml). The combined, dried extracts were concentrated in vacuo to give the title compound as a brown foam (940 mg).

n.m.r. (CDCl$_3$) δ 2.36 (3H,s), 2.48 (3H,s), 2.62 (4H,m), 3.10 (4H,m), 3.85 (3H,s), 6.70 (1H,d), 7.52 (1H,dd), 7.65 (1H,d), 7.78 (2H,m), 7.99 (1H,d).

INTERMEDIATE 60

1-(2-Bromo-5-nitrophenyl)-4-methylpiperazine

A suspension of 2-bromo-5-nitrobenzenamine (26.0 g) and 2-chloro-N-(2-chloroethyl)-N-methylethanamine hydrochloride (23.0 g) in chlorobenzene (150 ml) was treated according to the method of Intermediate 56. Purification by FCC eluting with System A (300:8:1 gradient to 200:8:1) gave the title compound as a brown solid (9.498 g) m.p. 100°–103° C.

INTERMEDIATE 61

4-Bromo-3-(4-methyl-1-piperazinyl)benzenamine

A suspension of Intermediate 60 (8.68 g) in ethanol (80 ml) and water (20 ml), under nitrogen, was treated with Raney nickel (~3 g of a slurry with water). The suspension was then cooled to 17° C. and maintained at a temperature below 28° C. during the careful, slow addition of hydrazine hydrate (6 ml), over 20 minutes. The cooled mixture was then stirred under nitrogen for 2 hours, then filtered through a pad of Hyflo. The combined filtrate and washings (ethanol:water; 6:1; 280 ml) were concentrated in vacuo to give a gummy solid which was dissolved in dichloromethane, dried and evaporated in vacuo to give a dark grey/brown solid. The solid was triturated in hexane:ether (1:1, 50 ml) overnight and the residue filtered and dried to give the title compound as a solid (3.28 g). Further product was obtained by concentration of the filtrate in vacuo. The resultant orange solid residue was purified by FCC eluting with System A (300:8:1) to give the title compound as a yellow solid (3.38 g). m.p. 120°–121.5° C.

EXAMPLE 1

N-[2-Methoxy-5-(4-methyl-1-piperazinyl)phenyl]-4-(4-pyridinyl)benzamide

A stirred mixture of Intermediate 4 (400 mg), 4-pyridinylboronic acid (122 mg) tetrakis(triphenylphosphine)palladium (0) (58 mg), and anhydrous sodium carbonate (115 mg) in water (18 ml) and DME (18 ml) was heated at reflux under nitrogen for 24 h. Further 4-pyridinylboronic acid (61 mg) was added and refluxing continued for a further 4 h. The reaction mixture was poured into 2N sodium carbonate (30 ml) and extracted with dichloromethane (3×75 ml). The dried extracts were evaporated in vacuo to give a brown oil (500 mg). This was chromatographed on silica (Merck 7729, 30 g) eluting with System A (200:8:1) to give the title compound as a yellow crystalline solid (147 mg).

T.l.c. System A (100:8:1) Rf 0.42.

n.m.r. (CDCl$_3$) δ2.37 (3H,s), 2.6 (4H,m), 3.2 (4H,m), 3.9 (3H,s), 6.66 (1H,dd), 6.87 (1H,d), 7.78 (2H, ½ AA'BB'), 8.02 (2, ½ AA'BB'), 8.38 (1H,d), 8.62 (1H, br.s), 8.72 (2H, ½ AA'BB').

Similarly prepared:

EXAMPLE 2

N-[4-Methoxy-3-(4-methyl-1-piperazinyl)phenyl]-4-(4-pyridinyl) benzamide as a yellow solid (90 mg), m.p. 183°–185° C.

Analysis Found: C,71.3; H,6.55; N,13.6. C$_{24}$H$_{26}$N$_4$O$_2$ 0.07 CH$_3$CO$_2$C$_2$H$_5$ requires C,71.4; H,6.55; N,13.7%.

From Intermediate 7 (0.160 g) and 4-pyridinylboronic acid (0.054 g). Purification by SPC eluting with System A (96:4:0.4) afforded the title compound.

EXAMPLE 3

4-(4-Pyridinyl)-2-methoxy-N-[4-methoxy-3-(4-methyl-1-piperazinyl) phenyl]benzamide A mixture of Intermediate 8 (532 mg) and 4-pyridinylboronic acid (272 mg) in DME (18 ml) was treated with a solution of sodium carbonate (351 mg) in water (9 ml) followed by tetrakis (triphenylphosphine)-palladium (0) (51 mg) and the mixture stirred at reflux under nitrogen for 10 h. The mixture was evaporated, treated with water (40 ml) and extracted with ethyl acetate (6×50 ml). The aqueous phase was filtered and the precipitate collected to give solid (I). The combined, dried organic extracts were evaporated and the residue combined with solid (I). The combined product was purified by FCC eluting with System A (945:50:5) to give the crude title compound (540 mg). This crystallised from ethyl acetate (10 ml) to give the pure title compound as pale cream crystals (204 mg).

T.l.c System A (89:10:1) Rf 0.26.

Analysis Found C,69,1;H.6.5;N,12.6; $C_{25}H_{28}N_4O_3$ requires C,69.4;H,6.5;N,12.95%

Similarly prepared:

EXAMPLE 4

N-[4-Hydroxy-3-(4-methyl-1-piperazinyl)phenyl]-4-(4-pyridinyl) benzamide as a white solid (85 mg) m.p. 157°-160° C.

T.l.c. System B (90:10:1) Rf =0.5.

From a mixture of Intermediate 9 (150 mg), 4-pyridinylboronic acid (50 mg), tetrakis(triphenylphosphine)palladium (0) (20 mg), DME (4ml) and sodium carbonate (2N; 1 ml). Purification by crystallisation from isopropanol afforded the title compound.

EXAMPLE 5

N-[4-Methoxy-3-(4-methyl-1-piperazinyl)phenyl]-4-(4-methyl-3-pyridinyl)benzamide as a cream-coloured foam (145 mg) m.p. 77°-81° C. T.l.c. System A (980:10:10), Rf=0.10.

From a mixture of Intermediate 7 (300 mg), Intermediate 10 (100 mg), sodium carbonate (2N; 2 ml), DME (8 ml) and tetrakis(triphenylphosphine)palladium (0) (50 mg). Purification by FCC eluting with System A (980:10:10→940:50:5) afforded the title compound.

EXAMPLE 6

N-[4-Methoxy-3-(4-methyl-1-piperazinyl)phenyl]-3-methyl-4-(4-pyridinyl)benzamide as a cream-coloured solid (241 mg) m.p. 208°-210° C.

Analysis Found: C,71.3; H,6.7;N,12.9; $C_{25}H_{28}N_4O_2 \cdot 0.34 H_2O$ requires C,71.0; H,6.8; N,13.2%

Water Assay Found: 0.10%w/w H2O =0.34 mol % H2O

From a mixture of Intermediate 11 (300 mg) 4-pyridinylboronic acid (88 mg) sodium carbonate (2N, 2 ml), DME (8 ml) and tetrakis (triphenylphosphine)palladium (0) (50 mg). Purification by FCC eluting with System B (980:10:10) afforded the title compound.

EXAMPLE 7

N-[3,4-Dimethoxy-5-(4-methyl-1-piperazinyl)phenyl]-4-(4-pyridinyl)benzamide

A mixture of Intermediate 18 (208 mg), 4-pyridinylboronic acid (59 mg), sodium carbonate (167 mg) and tetrakis(triphenylphosphine)palladium (0) (27 mg) in 1:1 aqueous DME (18 ml) was heated to reflux for 6 h. The mixture was allowed to cool, silica gel (Merck 9385, 5 g) was added, and the solvents evaporated. The residue was chromatographed eluting with System A (200:8:1) to give the title compound as an off-white solid (112 mg), m.p. 219°-221°.

Assay Found: C,68.9; H,6.65; N,12.5; $C_{25}H_{28}N_4O_3$ requires C,69.4; H, 6.55; N,12.95%

EXAMPLE 8

N-[4-Methoxy-3-(1-piperazinyl)phenyl]-4,(4-pyridinyl)-benzamide

A mixture of Intermediate 23 (550 mg), hydrochloric acid (3N; 10 ml), and ethyl acetate (50 ml) was stirred at room temperature for 4 h. The resulting solution was treated with aqueous sodium carbonate (2N; 25 ml) and extracted with dichloromethane (5×50 ml). The dried extract was evaporated and the residue was purified on a column of silica eluting with System B (90:10:1) to give the title compound as a yellow solid (200 mg), m.p. 77°-79°.

T.l.c. System B (90:10:1), Rf 0.2.

EXAMPLE 9

N-[3-(4-Ethyl-1-piperazinyl)-4-methoxyphenyl]-4-(4-pyridinyl)benzamide

A mixture of the product of Example 8 (110 mg), acetaldehyde (34 mg), acetic acid (72 mg) and methanol (5 ml) was stirred for 10 min under nitrogen at room temperature. The resulting brown solution was treated in one portion with sodium cyanoborohydride (25 mg) and stirred for 3 h. The mixture was basified with aqueous sodium carbonate (2N) and extracted with dichloromethane (3×50 ml). The dried extract was evaporated and the residue was purified twice on a column of silica eluting with System B (240:10:1) to give the title compound as a yellow foam (40 mg).

T.l.c. System B (90:10:1), Rf 0.5.

n.m.r (CDCl$_3$) δ1.15 (3H,t), 2.53 (2H,q), 2.68 (4H,br.s), 3.18 (4H, br.s), 3.88 (3H,s), 6.86 (1H,d), 7.22 (1H,d), 7.32 (1H,dd), 7.55 (2H, ½ AA'BB'), 7.76 (2H, ½ AA'BB'), 7.80 (1H,br.s), 8.0 (2H, ½ AA'BB'), 8.72 (2H, ½ AA'BB').

EXAMPLE 10

N-[2-Methoxy-3-(4-methyl-1-piperazinyl)phenyl]-4-(4-pyridinyl)benzamide

A mixture of Intermediate 37 (42 mg), 4-pyridinylboronic acid (19 mg) tetrakis(triphenylphosphine)palladium (0) (5 mg), aqueous sodium carbonate (2N;1 ml) and DME (4 ml) was refluxed under nitrogen for 18 h. The solution was added to water (25 ml) and extracted with dichloromethane (2×25 ml). The dried extract was evaporated and the residue was triturated with ether (2 ml) to give the title compound as a white powder (20 mg) m.p. 153°-155°.

Tlc System B (90:10:1) Rf 0.7.

Similarly prepared were:

EXAMPLE 11

N-[4-Methoxy-3-(4-methyl-1-piperazinyl)phenyl-2-methyl-4-(4-pyridinyl)benzamide as a white solid (110 mg) m.p. 183°-184° C.

T.l.c. System B (240:10:1) Rf=0.15

From a mixture of Intermediate 25 (200 mg), 4-pyridinylboronic acid (74 mg), tetrakis(triphenylphosphine)palladium (0) (10 mg), DME (8 ml), and aqueous sodium carbonate (2N; 2 ml). Purification by column chromatography eluting with System B (240:10:1) afforded the title compound.

EXAMPLE 12

2-Fluoro-N-[4-methoxy-3-(4-methyl-1-piperazinyl)-phenyl]4-(4-pyridinyl)benzamide as a yellow solid (160 mg) m.p. 203°-204° C.

T.l.c System B (240:10:1) Rf=0.2

From a mixture of Intermediate 26 (250 mg), 4-pyridinylboronic acid (74 mg), tetrakis(triphenylphosphine)palladium (0) (10 mg), aqueous sodium carbonate (2N; 2 ml), and DME (8 ml). Purification by column chromatography eluting with System B (240:10:1) afforded the title compound.

EXAMPLE 13

N-[3-(4-Methyl-1-Piperazinyl)phenyl]-4-(4-pyridinyl)-benzamide

A solution of Intermediate 33 (277 mg), in DME (8 ml) and 2N sodium carbonate (2 ml) containing tetrakis(triphenylphosphine)palladium (0) (20 mg) was treated with 4-pyridinylboronic acid (100 mg). The resulting mixture was stirred under nitrogen for 10min, then heated to reflux for 5 h before cooling to room temperature and standing overnight. The mixture was then added to water (50 ml) and extracted with dichloromethane (3x50 ml) then dichloromethane:ethanol (10:1) (50 ml). The combined, dried extracts were concentrated in vacuo to give a fine white powder-like solid which was purified by FCC eluting with System A (200:8:1) to give the title compound as a yellow solid, which was dried in vacuo at 60° C. for 22 h (109 mg) m.p. 232°-233° C.

T.l.c. System A (150:8:1) Rf=0.05

Similarly prepared was:

EXAMPLE 14

N-[4-Methyl-3-(4-methyl-1-piperazinyl)phenyl]-4-(4-pyridinyl)benzamide as a cream-coloured crystalline solid (160 mg) m.p. 225°-226° C.

Analysis Found: C,73.8; H,6.9; N,13.8; $C_{24}H_{26}N_4O.0.12C_2H_6O$ requires C,74.3; H,6.9; N,14.2% N.m.r.—0.12mol ethanol present per mol compound From a solution of Intermediate 32 (287 mg) in DME (8 ml) and 2N sodium carbonate ( 2 ml ) containing tetrakis (triphenylphosphine) palladium (0) (20 mg), treated with 4-pyridinylboronic acid (100 mg).

EXAMPLE 15

3-Methoxy-N-[4-methoxy-3-(4-methyl-1-piperazinyl)-phenyl]-4-(4-pyridinyl)benzamide A suspension of Intermediate 39 (300 mg) in thionyl chloride (5 ml) was heated to reflux under nitrogen for 1 h. After this time complete solution of material was seen and a yellow solid precipitated over the next 30min. Excess thionyl chloride was removed in vacuo to leave a pale yellow solid—the acid chloride—which was added to a solution of Intermediate 6 (290 mg) in dry pyridine (5 ml). The mixture was stirred at room temperature for 1 h and then concentrated in vacuo to give a dark yellow solid residue which was dissolved in water (50 ml) and extracted with dichloromethane (3×50 ml). The combined, dried extracts were concentrated in vacuo and purified by FCC eluting with System A (250:8:1) to give a yellow solid which was dried in vacuo at 60° C. to give a yellow solid. Recrystalliation from isopropanol (4 ml) afforded the title compound as a pale yellow crystalline solid (220 mg), m.p. 196°-197° C., after drying in vacuo at 60°-80° C. for 15 h.

Analysis Found: C,68.8; H,6.5; N,12.6; $C_{25}H_{28}N_4O_{3.0.45}C_3H_8O$ requires C,68.9; H,6.9; N,12.2%

N.m.r.—contains 0.45mol of isopropanol per mol compound

EXAMPLE 16

N-[4-Chloro-3-(4-methyl-1-piperazinyl)phenyl]-4-(4-pyridinyl)benzamide

A mixture of Intermediate 44 (250 mg) in DME (8 ml) and 2N sodium carbonate (2 ml) containing tetrakis(triphenylphosphine)palladium (0) (20 mg) was treated with 4-pyridinylboronic acid (100 mg) under nitrogen and stirred for 10min before heating to reflux for 1.5 h. The reaction mixture was then cooled to room temperature, added to water (25 ml) and extracted with dichloromethane (3×25 ml). The combined, dried extracts were concentrated in vacuo to give a yellow oil (343 mg) which crystallised on standing overnight. The solid was dissolved in ethanol and concentrated in vacuo onto silica (Merck 9385). Purification by FCC eluting with System A (125:8:1) gave a pale yellow foam which was triturated with ether to give the title compound as a cream-coloured solid (202 mg), m.p. 218°-219° C.

Analysis Found: C,67.8; H,5.9; N,13.3; $C_{23}H_{23}ClN_4O.0.15(CH_3CH_2)_2O$ requires C,67.7; H,5.8; N,13.6%

N.m.r. indicates 0.15mol ether per mol of compound. Similarly prepared were:

EXAMPLE 17

N-[4-Fluoro-3-(4-methyl-1-piperazinyl)phenyl]-4-(4-pyridinyl)benzamide as an off-white solid (215 mg) m.p. 205°-206° C.

Analysis Found: C,70.9; H,6.3; N,13.65; $C_{23}H_{23}FN_4O.0.35C_4H_{10}O$ requires C,70.4; H,6.4; N,13.45% n.m.r. indicated 0.35 mol ether per mol compound

From a mixture of Intermediate 45 (250 mg) in DME (8 ml) and 2N sodium carbonate (2 ml) containing tetrakis(triphenylphosphine)palladium (0) (20 mg) treated with 4-pyridinylboronic acid (90 mg).

EXAMPLE 18

N-[4-Butoxy-3-(4-methyl-1-piperazinyl)phenyl]-4-(4-pyridinyl)benzamide as a pale yellow powder (296 mg) m.p. 205°-207° C.

T.l.c. System A (75:8:1) Rf=0.25.

From a stirred solution of Intermediate 49 (316 mg) in DME (8 ml) containing 2N sodium carbonate (2 ml) and tetrakis(triphenylphosphine)palladium (0) (20 mg), treated with 4-pyridinylboronic acid (100 mg).

EXAMPLE 19

N-[4-Methoxy-3-(4-methyl-1-piperazinyl)]-4-(3-methyl-4-pyridinyl)benzamide as a pale yellow foam (66 mg)

Analysis Found: C,69.4; H,6.6; N,12.6; $C_{25}H_{28}N_4O_2.0.8H_2O$ requires C,69.7; H,6.9; N,13.0% n.m.r. ($CDCl_3$) $\delta2.28+2.38$ (6H, 2xs), 2.63 (4H,br.m), 3.15 (4H,br.m), 3.88 (3H,s), 6.87 (1H,d), 7.16 (1H,d), 7.2-7.35 (2H,m), 7.44 (2H, ½ AA'BB'), 7.79 (1H,br.s), 7.97 (2H, ½ AA'BB'), 8.48-8.52 (2H, br.s).

From a solution of 4-bromo-3-methylpyridine hydrochloride (777 mg) in water (3 ml), treated with sodium hydrogen carbonate until effervescence stopped. The solution was then treated with 2N sodium carbonate (2 ml), DME (10 ml), tetrakis(triphenylphosphine)palladium (0) (100 mg) and Intermediate 54 (430 mg).

EXAMPLE 20

N-[6-Fluoro-4-methoxy-3-(4-methyl-1-piperazinyl)-phenyl]-3-methyl-4-(4-pyridinyl)benzamide as off-white crystals (173 mg) m.p. 92°–93° C.

Analysis Found: C,62.9; H,6.2; N,11.4; $C_{25}H_{27}FN_4O_2$ 2.4H$_2$O requires C,62.8; H,6.7; N,11.7%

From a solution of Intermediate 59 (405 mg) in DME (12 ml) and 2N sodium carbonate (3 ml), treated with 4-pyridinylboronic acid (115 mg) and tetrakis(triphenylphosphine)palladium (0) (30 mg).

EXAMPLE 21

2-Hydroxy-N-[4-methoxy-3-(4-methyl-1-piperazinyl)-phenyl]-4-(4-methyl-3-pyridinyl)benzamide A mixture of Intermediate 51 (250 mg), Intermediate 50 (91 mg), tetrakis(triphenylphosphine)palladium (0) (10 mg), aqueous sodium carbonate (2N;2 ml), and DME (10 ml) was refluxed for 16 h under nitrogen. The cooled mixture was added to water (30 ml) and extracted with dichloromethane:methanol (19:1) (3×100 ml). The dried extract was evaporated and the residue was purified by FCC eluting with System B (240:10:1) to give a yellow foam. The foam was triturated with ether (2 ml) to give the title compound as a white foam (75 mg).

T.l.c. System B (90:10:1) Rf 0.5.

n.m.r. (CDCl$_3$) δ2.32+2.38 (6H, 2xs), 2.67 (4H,m), 3.15 (4H,br.m), 3.89 (3H,s), 5.2(1H,vbr.s), 6.88 (2H,d+dd), 6.99 (1H,d), 7.12 (1H,d), 7.22 (1H,br.d), 7.30 (1H,dd), 7.75 (1H,d), 8.45–8.55 (3H, vbr.s+br.s+br.d).

EXAMPLE 22

N-[4-Bromo-3-(4-methyl-1-piperazinyl)phenyl]-3-methyl-4-(4-pyridinyl)benzamide

A solution of Intermediate 61 (150 mg) in dimethyl sulphoxide (1 ml), was treated under nitrogen at room temperature with sodium hydride (30 mg, 60% dispersion in oil) and stirred for 10 minutes. The mixture was then treated with a solution of Intermediate 53 (152 mg) in dimethyl sulphoxide (0.5 ml). The mixture was stirred at room temperature for 2 days before adding additional Intermediate 53 (30 mg). The mixture was poured into water (3 ml) and extracted with dichloromethane (2×4 ml). The combined, dried extracts were concentrated in vacuo to give a yellow oil which was triturated in ether to give the title compound as a cream-coloured powdery solid (116 mg) m.p. 240°–241° C.

Analysis Found: C,61.8; H,5.4; N, 11.85; $C_{24}H_{25}BrN_4O$ Requires: C,61.9; H, 5.4; N, 12.0%

The following examples illustrate pharmaceutical formulations according to the invention. The term "active ingredient" is used herein to represent a compound of formula (I).

PHARMACEUTICAL EXAMPLE 1

| Oral Tablet A | |
|---|---|
| Active Ingredient | 700 mg |
| Sodium starch glycollate | 10 mg |
| Microcrystalline cellulose | 50 mg |

| -continued | |
|---|---|
| Oral Tablet A | |
| Magnesium stearate | 4 mg |

Sieve the active ingredient and microcrystalline cellulose through a 40 mesh screen and blend in a appropriate blender. Sieve the sodium starch glycollate and magnesium stearate through a 60 mesh screen, add to the powder blend and blend until homogeneous. Compress with appropriate punches in an automatic tablet press. The tablets may be coated with a thin polymer coat applied by the film coating techniques well known to those skilled in the art. Pigments may be incorporated in the film coat.

PHARMACEUTICAL EXAMPLE 2

| Oral Tablet B | |
|---|---|
| Active Ingredient | 500 mg |
| Lactose | 100 mg |
| Maize Starch | 50 mg |
| Polyvinyl pyrrolidone | 3 mg |
| Sodium starch glycollate | 10 mg |
| Magnesium stearate | 4 mg |
| Tablet Weight | 667 mg |

Sieve the active ingredient, lactose and maize starch through a 40 mesh Screen and blend the powders in a suitable blender. Make an aqueous solution of the polyvinyl pyrrolidone (5–10% w/v). Add this solution to the blended powders and mix until granulated; pass the granulate through a 12 mesh screen and dry the granules in a suitable oven or fluid bed dryer. Sieve the remaining components through a 60 mesh screen and blend them with the dried granules. Compress, using appropriate punches, on an automatic tablet press.

The tablets may be coated with a thin polymer coat applied by film coating techniques well known to those skilled in art. Pigments may be incorporated in the film coat.

PHARMACEUTICAL EXAMPLE 3

| Inhalation Cartridge | |
|---|---|
| Active Ingredient | 1 mg |
| Lactose | 24 mg |

Blend active ingredient, particle size reduced to a very fine particle size (weight mean diameter ca. 5 μm) with the lactose in a suitable powder blender and fill the powder blender into No. 3 hard gelatin capsules.

The contents of the cartridges may be administered using a powder inhaler.

PHARMACEUTICAL EXAMPLE 4

| Injection Formulation | % w/v |
|---|---|
| Active ingredient | 1.00 |
| Water for injections B.P. to | 100.00 |

Sodium chloride may be added to adjust the tonicity of the solution and the pH may be adjusted to that of maximum stability and/or to facilitate solution of the active ingredient using dilute acid or alkali or by the addition of suitable buffer salts. Antioxidants and metal chelating salts may also be included.

We claim:

1. A compound of formula (I):

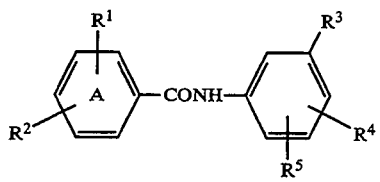

or a physiologically acceptable salt or solvate thereof wherein
R$^1$ represents a hydrogen atom, a halogen atom or a group selected from C$_{1-6}$alkyl and C$_{1-6}$alkoxy;
R$^2$ represents a pyridinyl group optionally substituted by one or two substituents selected from halogen atoms, C$_{1-6}$alkyl, hydroxyC$_{1-6}$alkyl, C$_{1-6}$alkoxyC$_{1-6}$alkyl, C$_{1-6}$alkoxy, hydroxy, —CN, —NO$_2$, —CO$_2$R$^6$, —COR$^6$, —CONR$^6$R$^7$ and —(CH$_2$)$_m$OC(O)C$_{1-4}$alkyl;
R$^3$ represents the group

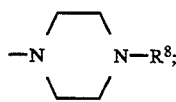

R$^4$ and R$^5$, which may be the same or different, each independently represent a hydrogen atom or a halogen atom or a group selected from hydroxy, C$_{1-6}$alkoxy and C$_{1-6}$alkyl; R$^6$, R$^7$ and R$^8$, which may be the same or different, each independently represent a hydrogen atom or a C$_{1-6}$alkyl group; and m represents zero or an integer from 1 to 3.

2. A compound according to claim 1 wherein R$^2$ represents a 3- or 4-pyridinyl group, optionally substituted by one or two substituents selected from halogen atoms, C$_{1-6}$alkyl, hydroxyC$_{1-6}$alkyl, C$_{1-6}$alkxylC$_{1-6}$alkyl, C$_{1-6}$alkoxy, hydroxy, —CN, NO$_2$, —CO$_2$R$^6$, —COR$^6$, CONR$^6$R$^7$ and —(CH$_2$)$_m$OC(O)C$_{1-4}$alkyl.

3. A compound according to claim 1 wherein R$^2$ represents a pyridinyl group optionally substituted by a single substituent selected from halogen atoms, C$_{1-6}$alkyl, hydroxyC$_{1-6}$alkyl, C$_{1-6}$alkoxyC$_{1-6}$alkyl C$_{1-6}$alkoxy, hydroxy, —CN, —NO$_2$, —CO$_2$R$^6$, —COR$^6$, —CONR$^6$R$^7$ and —(CH$_2$)$_m$OC(O)C$_{1-4}$alkyl.

4. A compound according to claim 3 wherein the single substituent on the pyridinyl group is in a position ortho to the bond to the phenyl ring A in general formula (I).

5. A compound according to claim 1 wherein R$^1$ is a hydrogen atom, a halogen atom, or a group selected from C$_{1-3}$alkyl, and C$_{1-3}$alkoxy.

6. A compound according to claim 1 wherein R$^4$ is attached at the para-position relative to the amide linkage.

7. A compound according to claim 1 wherein R$^4$ represents a hydrogen atom or a halogen atom or a hydroxy, C$_{1-3}$alkoxy, or C$_{1-3}$alkyl group.

8. A compound according to claim 1 wherein R$^5$ is a hydrogen atom or a C$_{1-6}$alkoxy group.

9. A compound according to claim 1 wherein R$^8$ is a hydrogen atom or a C$_{1-3}$alkyl group.

10. A compound of formula (I)

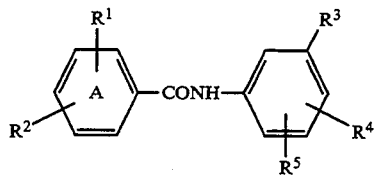

or a physiologically acceptable salt or solvate thereof wherein
R$^1$ represents a hydrogen atom, a halogen atom or a group selected from C$_{1-6}$alkyl and C$_{1-6}$alkoxy;
R$^2$ represents a pyridinyl group optionally substituted by a C$_{1-6}$alkyl group;
R$^3$ represents the group

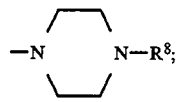

R$^4$ and R$^5$, which may be the same or different each independently represent a hydrogen atom or a halogen atom or a group selected from hydroxy and C$_{1-6}$alkoxy; and
R$^6$, R$^7$ and R$^8$, which may be the same or different, each independently represent a hydrogen atom or a C$_{1-6}$alkyl group.

11. The compound:
N-[4-methoxy-3-(4-methyl-1-piperazinyl)phenyl]-3-methyl-4-(4-pyridinyl)benzamide, and physiologically acceptable salts and solvates thereof.

12. A compound selected from:
N-[4-methoxy-3-(4-methyl-1-piperazinyl)phenyl]-4-(4-pyridinyl) benzamide;
N-[4-methoxy-3-(4-methyl-1-piperazinyl)phenyl]-4-(4-methyl-3-pyridinyl)benzamide;
N-[4-methoxy-3-(4-methyl-1-piperazinyl)phenyl]-2-methyl-4-(4-pyridinyl)benzamide;
N-[4-methyl-3-(4-methyl-1-piperazinyl)phenyl]-4-(4-pyridinyl)benzamide;
N-[4-chloro-3-(4-methyl-1-piperazinyl)phenyl]-4-(4-pyridinyl)benzamide;
N-[4-fluoro-3-(4-methyl-1-piperazinyl)phenyl]-4-(4-pyridinyl)benzamide;
N-[4-methoxy-3-(4-methyl-1-piperazinyl)]-4-(3-methyl-4-pyridinyl)benzamide;
N-[6-fluoro-4-methoxy-3-(4-methyl-1-piperazinyl)phenyl]-3-methyl-4-(4-pyridinyl)benzamide;
N-[4-bromo-3-(4-methyl-1-piperazinyl)phenyl]-3-methyl-4-(4-pyridinyl)benzamide;
N-[3-(4-methyl-1-piperazinyl)phenyl]-4-(4-pyridinyl)benzamide;
4-(4-pyridinyl)-2-methoxy-N-[4-methoxy-3-(4-methyl-1-piperazinyl)phenyl]benzamide;
N-[4-hydroxy-3-(4-methyl-1-piperazinyl)phenyl]4-(4-pyridinyl)benzamide;
and physiologically acceptable salts and solvates thereof.

13. A compound according to claim 2 wherein R$^2$ is an optionally substituted 4-pyridinyl group.

14. A compound according to claim 3 wherein $R^2$ represents a pyridinyl group optionally substituted by a $C_{1-6}$alkyl group.

15. A compound according to claim 3 wherein $R^2$ represents a pyridinyl group optionally substituted by a methyl group.

16. A compound according to claim 14 wherein the $C_{1-6}$alkyl substituent on the pyridinyl group is in a position ortho to the bond to the phenyl ring A in formula (I).

17. A compound according to claim 15 wherein the methyl substituent on the pyridinyl group is in a position ortho to the bond to the phenyl ring A in formula (I).

18. A compound according to claim 5 wherein R' represents fluorine, methyl or methoxy.

19. A compound according to claim 7 wherein $R^4$ represents fluorine, chlorine, methoxy or methyl.

20. A compound according to claim 8 wherein $R^5$ represents a methoxy group.

21. A compound according to claim 9 wherein $R^8$ represents a methyl group.

22. A pharmaceutical composition for use in the treatment or prophylaxis of depression comprising an effective amount of at least one compound of formula (I) as defined in claim 1 or a physiologically acceptable salt or solvate thereof, together with at least one physiologically acceptable carrier or excipient.

23. A pharmaceutical composition for use in the treatment of Parkinson's disease comprising an effective amount of at least one compound of formula (I) as defined in claim 1 or a physiologically acceptable salt of solvate thereof, together with at least one physiologically acceptable carrier or excipient.

* * * * *